(12) United States Patent
Baird et al.

(10) Patent No.: US 11,162,944 B2
(45) Date of Patent: Nov. 2, 2021

(54) COMPOSITIONS AND METHODS

(71) Applicant: Diagnostig LTD., Bangor Gwynedd (GB)

(72) Inventors: Mark Stephen Baird, Bangor Gwynedd (GB); Christopher David Gwenin, Bangor Gwynedd (GB); Juma'a Raheem Najeem Al-Dulayymi, Bangor Gwynedd (GB); Mohsin Omar Mohammed, Bangor Gwynedd (GB)

(73) Assignee: DIAGNOSTIG LTD., Bangor Gwynedd (GB)

( * ) Notice: Subject to any disclaimer, the term of this patent is extended or adjusted under 35 U.S.C. 154(b) by 99 days.

(21) Appl. No.: 15/752,037

(22) PCT Filed: Aug. 12, 2016

(86) PCT No.: PCT/GB2016/052508
§ 371 (c)(1),
(2) Date: Feb. 12, 2018

(87) PCT Pub. No.: WO2017/025757
PCT Pub. Date: Feb. 16, 2017

(65) Prior Publication Data
US 2018/0231547 A1    Aug. 16, 2018

(30) Foreign Application Priority Data

Aug. 13, 2015  (GB) .................................... 1514413

(51) Int. Cl.
| | | |
|---|---|---|
| *A61K 39/00* | (2006.01) |
| *A61K 39/02* | (2006.01) |
| *A61K 39/04* | (2006.01) |
| *G01N 33/569* | (2006.01) |
| *C07H 15/04* | (2006.01) |
| *C07H 15/18* | (2006.01) |
| *G01N 33/543* | (2006.01) |

(52) U.S. Cl.
CPC ......... *G01N 33/5695* (2013.01); *C07H 15/04* (2013.01); *C07H 15/18* (2013.01); *G01N 33/5432* (2013.01); *G01N 33/56933* (2013.01); *G01N 2333/30* (2013.01); *G01N 2333/35* (2013.01); *G01N 2469/20* (2013.01)

(58) Field of Classification Search
CPC ......... A61K 39/00; A61K 39/02; A61K 39/04
USPC .................. 424/234.1, 248.1; 435/4, 7.1, 7.2
See application file for complete search history.

(56) References Cited

FOREIGN PATENT DOCUMENTS

| | | | | |
|---|---|---|---|---|
| JP | 2004003912 | | | 1/2004 |
| JP | 2004003912 | A | * | 1/2004 |
| JP | 2004003912 | A | * | 1/2004 |
| JP | 2006312604 | | | 11/2006 |
| JP | 2006312604 | A | * | 11/2006 |
| JP | 20060312604 | A | * | 11/2006 |
| WO | 9820900 | | | 5/1998 |
| WO | 2016024118 | A1 | | 2/2016 |

OTHER PUBLICATIONS

Mohammed et al., "Arabino mycolates from synthetic mycolic acids," Tetrahedron 72 (2016), 2849-2857.
Mohammed et al., "Mycolyl arabino glycerols from synthetic mycolic acids," Tetrahedron Letters 56 (2015), 3268-3272.
International Search Report and Written Opinion issued in connection with corresponding PCT Application No. PCT/GB2016/052508 dated Nov. 7, 2016, 10 pages.
International Preliminary Report on Patentability issued in connection with International Application No. PCT/GB2016/052508 dated Feb. 13, 2018, 7 pages.

* cited by examiner

*Primary Examiner* — Rodney P Swartz
(74) *Attorney, Agent, or Firm* — Hoffman Warnick LLC

(57) ABSTRACT

A method of determining whether an individual is infected with a mycobacterial disease, the method comprising: (a) providing a system which comprises an antigen; (b) contacting the system with a sample obtained from the individual; and (c) detecting the presence or absence of binding of a biomarker in the sample with the antigen; wherein the antigen is an arabinose ester of a mycolic acid or an analogue thereof.

8 Claims, 2 Drawing Sheets

COMPOSITIONS AND METHODS

The present invention relates to a kit and method for determining whether or not an individual is infected with a mycobacterial disease and to compositions for use in the same and/or for treatment of diseases of the immune system.

Pathogenic and non-pathogenic mycobacteria are very widespread in the environment and their rapid detection and distinction represents an important public health target.

For example, tuberculosis is a serious and often fatal disease which affects humans and other animals and is caused by infection with mycobacteria. Infection with *Mycobacterium tuberculosis* is very common and it is estimated that up to a third of the world's population is infected with the bacterium. Most of those infected will never develop the active disease but because it is often fatal if left untreated, early diagnosis of the disease is essential. Methods of detecting *M. tuberculosis* are known but these existing methods have a number of disadvantages. It can often take a long time for the results of a test to be known, the equipment needed is expensive or difficult to use and the results are not always reliable and some methods are not able to distinguish between active and latent tuberculosis. A number of serodiagnostic assays have been developed for the rapid point of care diagnosis of tuberculosis but none of these have been assessed as reaching the standards required by the World Health Organisation.

Infection with tuberculosis is also common in cattle and bovine tuberculosis is recognised as a serious problem. Another disease common in cattle is Johne's disease which is caused by infection with another mycobacteria, *Mycobacterium avium* paratuberculosis. There have been some studies suggesting that Crohn's disease in humans may be linked to ingestion of food infected with *M. avium*.

Infectious diseases, for example tuberculosis, can cause a person or animal infected with the disease to produce antibodies. Identification of these antibodies in a sample taken from an infected individual can lead to a diagnosis of the disease.

However the diagnosis of infection with *Mycobacterium tuberculosis* is not straightforward, due to the complexity of the disease. Patients often present with co-infection with HIV and this can significantly change their blood biochemistry and the availability of sputum samples. People living in areas of the world where infection with mycobacteria is common have different background levels of antibodies in their blood and many will be infected with latent tuberculosis.

One problem with many diagnostic methods of the prior art is that they fail to distinguish between latent tuberculosis and active tuberculois disease. It can also be very difficult to diagnose tuberculosis in children.

In addition, infection with *Mycobacterium tuberculosis* can sometimes be difficult to rapidly differentiate from infection with other mycobacteria, for example *Mycobacterium avium*.

Due to these complexities it has been difficult to find a satisfactory method of accurately diagnosing infection with *Mycobacterium tuberculosis*. The current "gold standard" method of confirming infection with tuberculosis is by growing a culture from a sample. However this is a complex and expensive method and it can take a number of weeks to confirm a diagnosis. Thus culture methods are unsuitable for use in environments with limited access to laboratory facilities and in many cases a quick diagnosis is essential.

It is an aim of the present invention to provide a kit and method for detecting infection with Mycobacteria which is faster, less expensive and has improved reliability compared with methods of the prior art. It is also desirable to find a method which can reliably distinguish between infection with different types of mycobacteria.

BRIEF DESCRIPTION OF THE DRAWINGS

FIG. 2 again shows selective stimulation depending on the antigen structure.

DETAILED DESCRIPTION

Figure 1:
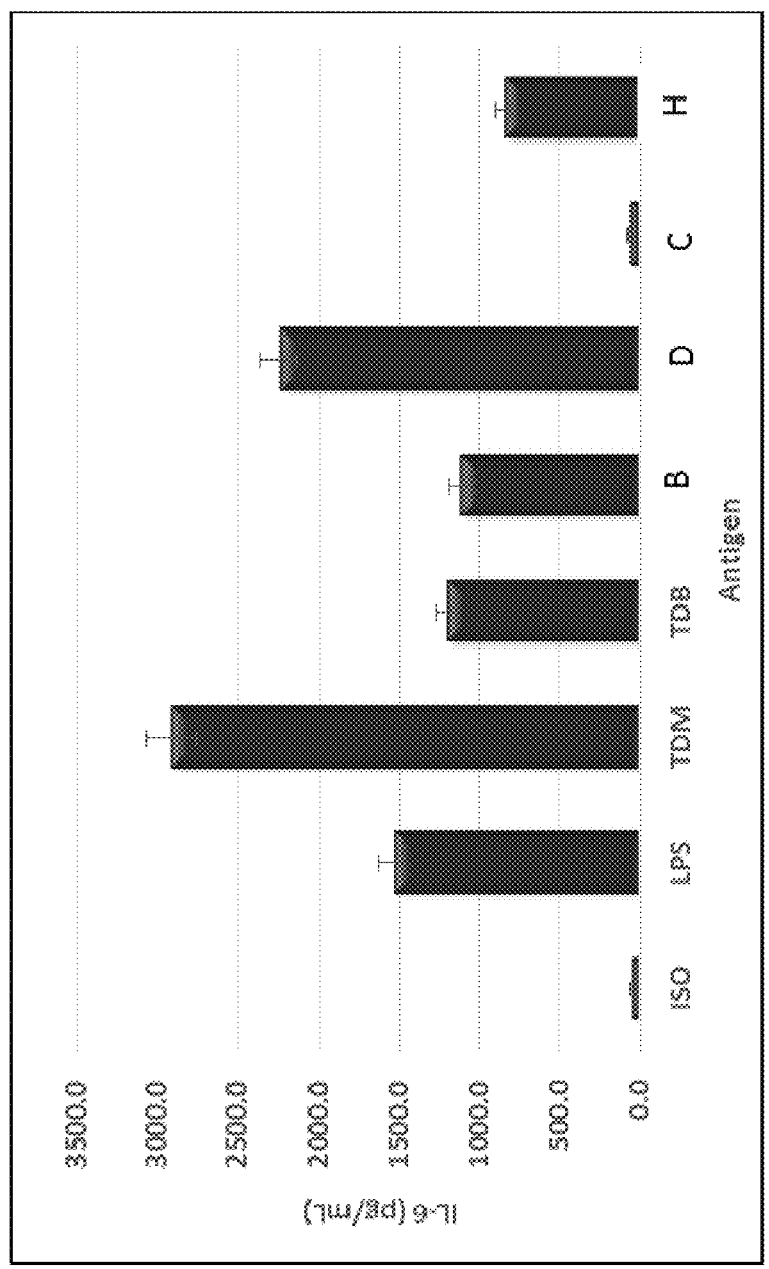
FIG. 1 shows the experimental results of measured IL-6 secretion by wild-type BMDCs from mice using compounds B, D, C and H as antigens and isopropyl alcohol (ISO) as a solvent. Commercial trehalose-6,6-dimycolate (TDM), lipopolysaccharides (LPS), and trehalose-6,6-dibehenate (TDB) were used as a controls.

According to a first aspect of the present invention, there is provided a method of determining whether an individual is infected with a mycobacterial disease, the method comprising:
(a) providing a system which comprises an antigen;
(b) contacting the system with a sample obtained from the individual; and
(c) detecting the presence or absence of binding of a biomarker in the sample with the antigen;
wherein the antigen is an arabinose ester of a mycolic acid or an analogue thereof.

Suitably steps (a), (b) and (c) are carried out in the order (a) followed by (b) followed by (c).

The method may additionally or alternatively provide a method of determining whether an individual is infected with organisms, other than mycobacteria, which produce mycolic acid related molecules.

The antigen may be present on a substrate in the system and/or in one or more solutions or suspensions in the system. The antigen may be encapsulated in the system, for example in liposomes.

If further antigens are present in the system, the sample may be brought into contact with the antigens individually in order to allow the detection of the presence or absence of the binding of a biomarker in the sample with each antigen separately.

In some embodiments, the antigen is bound to a substrate in the system. Suitably the system comprises at least one substrate.

The system may comprise more than one substrate. If further antigens are present in the system, each of the antigens may be each bound to different substrates.

Suitably the first aspect of the present invention provides a method of determining whether an individual is infected with a mycobacterial disease, the method comprising:
(a) providing a substrate which carries an antigen;
(b) contacting the substrate with a sample obtained from the individual;
(c) detecting the presence or absence of binding of a biomarker in the sample with the antigen;
wherein the antigen is an arabinose ester of a mycolic acid or an analogue thereof.

Suitably steps (a), (b) and (c) are carried out in the order (a) followed by (b) followed by (c).

The present invention provides a method of determining whether an individual is infected with a mycobacterial disease. The method involves detection of a biomarker in the sample that is indicative of infection with a mycobacterial disease. The biomarker is suitably an antibody.

The present invention preferably relates to a method of determining the presence or absence in a sample of an antibody indicative of infection with or exposure to mycobacteria. The sample may be taken form any individual suspected of infection with a mycobacterial disease. In preferred embodiments the individual is a mammal. It may be a ruminant, for example a cow. In some embodiments the individual is a human.

Suitably the invention involves determining the presence or absence of a disease antibody indicative of infection with any disease caused by infection with mycobacteria. Examples of such diseases include tuberculosis, leprosy, pulmonary disease, burili ulcer, Johne's disease and bovine tuberculosis.

In preferred embodiments the method of the present invention is used to determine the presence or absence of an antibody indicative of infection with *Mycobacterium tuberculosis* and/or *Mycobacterium avium* paratuberculosis.

The invention finds particular utility in determining the presence or absence in a sample of disease antibodies indicative of the presence of tuberculosis.

Step (a) of the method of the first aspect of the present invention may involve providing a substrate which carries the antigen.

The antigen is suitably immobilised on the surface of the substrate, for example as is further described herein.

Step (a) of the method of the first aspect of the present invention may involve providing a substrate which carries the arabinose ester of a mycolic acid or an analogue thereof.

The nature of the substrate will depend on the exact structure of the device. Suitable substrates are further described herein. For the avoidance of doubt the term substrate as used in relation to step (a) of the method of the first aspect refers to a carrier, for example a solid carrier, for the antigens. It is typically a plate or sheet-like material. In some embodiments the substrate is a gel.

The antigen is suitably immobilised on the surface of the substrate, for example as is further described herein.

Mycolic acids are long chain fatty acid compounds typically having 60 to 90 carbon atoms and are found as components of the cells of mycobacteria.

Two moieties can be distinguished in each mycolic acid: the main branch, or meromycolate moiety, and the mycolic motif, an α-alkyl β-hydroxy acid. The structure of the mycolic motif is common to each naturally occurring mycolic acid, except for minor variations in the length of the chain in the α-position. The two stereocentres in the α and β positions relative to the carboxylic group present in all natural mycolic acids have, when examined, always been found to both be in the (R)-configuration in these natural products. On the other hand, the meromycolate section, which generally contains two functionalities and three long chains (a, b, c in formula I), can be differently substituted in both the proximal (the one nearer the hydroxy-acid) and the distal position (further from the carboxylic acid).

Formula 1

α-Mycolic acid

The mycolic acids are broadly separated into classes, according to the groups present in the meromycolate moiety. The proximal or distal functional groups can include cyclopropanes, double bonds, an epoxy group, a methoxy group, carbonyl group, carboxyl group or methyl group.

Mycolic acid wax esters are compounds having a similar structure to the above mycolic acids but including an ester functionality in the main chain. These compounds are found naturally in the bacterial cell walls of *Mycobacterium avuim* and a range of other mycobacteria.

The antigen used in the method of the present invention is an arabinose ester of a mycolic acid or a derivative or analogue thereof. By this we mean to include any compound which contains both an arabinose unit and a mycolic acid unit or an analogue of a mycolic acid.

Suitably the antigen is selected from an arabinose ester of a mycolic acid, an arabinose ester of a wax ester and an arabinose ester of a fatty acid analogue of a mycolic acid.

In some embodiments the antigen for use herein is a compound of formula (III):

$$(M)_x\text{-}(S)_y\text{-}(M')_z \quad (III)$$

wherein x is from 1 to 6, y is from 1 to 12, z is from 0 to 10, each M and each M' is independently a mycolic acid moiety including a β-hydroxy acid moiety and each S is a monosaccharide unit, provided that at least one S is an arabinose unit.

In some embodiments x is from 1 to 4, preferably from 1 to 3, more preferably x is 1 or 2 and most preferably x is 1.

When x is greater than 1 and y is greater than 1, each M may be bonded to the same or different monosaccharide unit.

In some embodiments z is 0 to 6, preferably 0 to 4, more preferably 0 to 2, for example 0 or 1. In some embodiments preferably z is 1.

When z is greater than 1 and y is greater than 1, each M' may be bonded to the same or different monosaccharide unit.

Each M or M' is a mycolic acid residue. By this we mean to refer to the portion of the acid molecule other than the acidic proton.

Each M and M' may be the same or different. When x is greater than 1, each M may be the same or different. When z is greater than 1, each M' may be the same or different.

The compounds of formula (III) are sugar esters of mycolic acid. Thus each acidic unit of the mycolic acid residues M and/or M' is bonded to an alcoholic group of a monosaccharide unit to form an ester linkage. Preferably each M and/or M' is bonded to a primary alcoholic group of a monosaccharide unit.

Suitable sugar ester compounds include monomycolates, dimycolates, trimycolates and tetramycolates; and mixed esters of sugars and alcohols (i.e. where some mycolic acid moieties are esterified by reaction with a sugar group and some by reaction with a simple alcohol).

In some embodiments y is between 1 and 6, preferably between 1 and 4, more preferably between 1 and 3. In some embodiments most preferably y is 1 or 2, especially 2.

In some embodiments the compound of formula (III) is an ester formed from one mycolic acid unit and one monosaccharide unit, i.e. an arabinose unit.

In some embodiments, the compound of formula (III) is an ester formed from one mycolic acid unit and two monosaccharide units wherein the two monosaccharide units are joined to form a disaccharide. Thus in such embodiments the compound of formula (III) is an ester formed from one mycolic acid unit and a disaccharide. The disaccharide moiety may be a diarabinose unit or it may contain arabinose and a different monosaccharide.

In some preferred embodiments, the compound of formula (III) is an ester formed from two mycolic acid units and two monosaccharides, that is two mycolic acid units and a disaccharide. In such cases, the compound has the formula M-S-S-M' in which each monosaccharide unit S may be the same or different.

In some preferred embodiments the ratio of mycolic acid units (M and M' combined total) to monosaccharide units(s) is approximately 1:1.

In some embodiments x+z=y.

Preferably the or each monosaccharide unit S has from 3 to 8 carbon atoms, preferably 5 or 6. In some embodiments the or each antigen includes a monosaccharide unit having 6 carbon atoms. In some embodiments the or each antigen includes a monosaccharide unit S which is an aldose.

Suitable aldose units include allose, altrose, galactose, glucose, gulose, idose, mannose, talose, fructose, psicose, sorbose, and tagatose. Preferred aldoses include allose, altrose, galactose, glucose, gulose, idose, mannose and talose. In some embodiments the or each antigen includes a glucose and/a mannose unit. In some embodiments each antigen includes a glucose unit.

In some preferred embodiments each S is an arabinose unit.

Each monosaccharide unit may be present as the D or L isomer. Preferably each is present as the natural D isomer. Each monosaccharide unit may be present as the α form or the β form.

In some embodiments, y is 2 and the compound of formula (III) includes a disaccharide unit. In such a disaccharide unit, the monosaccharides may be connected in any suitable way. As the skilled person will appreciate, the nature of the bonding between the two monosaccharide units will determine the nature of the disaccharide.

Each S is a monosaccharide unit. By monosaccharide unit we mean to include monosaccharide moieties in which all the non-bonded hydroxyl groups are free hydroxyl groups. However in some monosaccharide groups one or more hydroxyl groups may be protected. Suitable protecting groups are known to the person skilled in the art.

Arabinose has the structure:

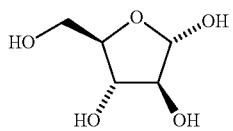

In some embodiments the arabinose unit may itself be substituted. In some preferred embodiments one of the alcohol groups has reacted to form an ether.

In some preferred embodiments the antigen is a monomycolate of an arabinose ester which has an alkoxy substituent at the anomeric position. Thus the antigen may be a compound of formula (IV):

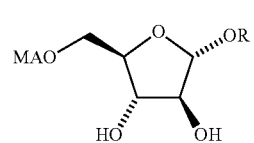

(IV)

wherein MA is the residue of a mycolic acid or an analogue thereof and R is an alkyl group. Preferably R is a $C_1$ to $C_4$ alkyl group. Most preferably R is methyl or ethyl.

Each M or M' in formula (III) and MA in formula (IV) is a mycolic acid residue or an analogue thereof. Suitable analogues of mycolic acids include mycolic acid wax esters, long chain fatty acid compounds and β-hydroxy acids.

Suitable mycolic acid classes for use in the preparation of antigens include keto mycolic acids having the structure shown in formula IIa; hydroxy mycolic acids having the structure shown in formula IIb; alpha mycolic acids having the structure shown in formula IIc; and methoxy mycolic acids having the structure shown in formula IId. Such mycolic acids may be used directly as the free acid or as an ester or salt thereof.

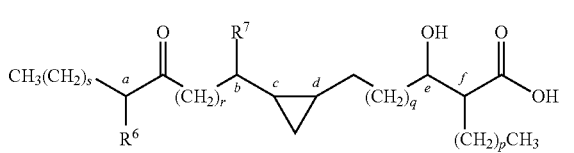

IIa

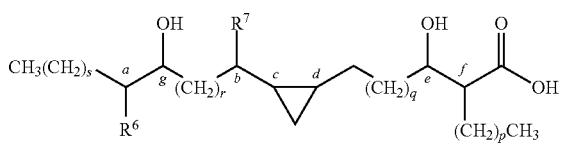

IIb

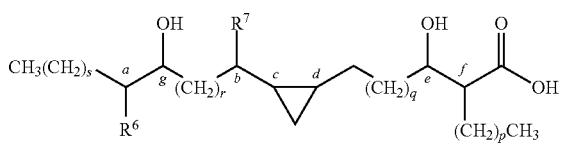

IIc

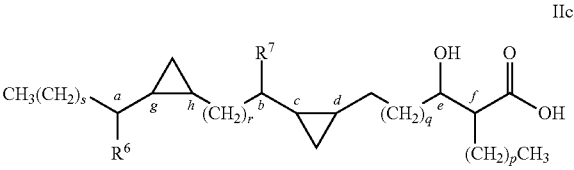

IId

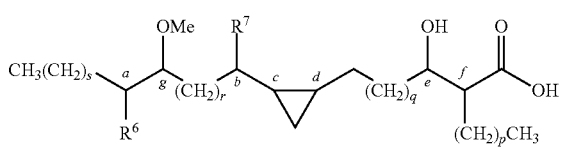

In each of the structures IIa, IIb, IIc and IId $R^6$ may be hydrogen or $C_1$ to $C_4$ alkyl. Preferably $R^6$ is hydrogen or methyl.

In each of the structures IIa, IIb, IIc and IId $R^7$ may be hydrogen or $C_1$ to $C_4$ alkyl. Preferably $R^7$ is hydrogen or methyl.

In each of the structures IIa, IIb, IIc and IId p is preferably from 4 to 40, preferably from 8 to 36, more preferably from 12 to 32, for example from 16 to 30, more preferably from 20 to 28, for example from 22 to 26.

In the structures IIa, IIb, IIc and IId q is preferably from 2 to 40, more preferably from 4 to 36, for example from 6 to 30, preferably from 8 to 24, for example from 10 to 20 and preferably from 12 to 18.

In the structures IIa, IIb, IIc and IId, r is preferably from 2 to 40, for example from 6 to 36, preferably from 10 to 32, for example from 12 to 28, and preferably from 14 to 24.

In the structures IIa, IIb, IIc and IId, s is preferably from 2 to 40, for example from 6 to 36, preferably from 10 to 32, for example from 12 to 28, and preferably from 14 to 24.

In the structures IIa, IIb, IIc and IId, each of the chiral centres indicated at a, b, c, d, e, f, g and h may independently have either an (R) or an (S) configuration. Each cyclopropyl group may have either absolute stereochemistry and may have a trans or a cis configuration.

Any of the stereocentres indicated by a, b, c, d, e, f, g or h may be racemic. In the case of structure IIa it is possible that the stereocentre designated a will be racemic as this is a readily epimerisable position.

In addition to the compounds illustrated by the structures IIa, IIb, IIc and IId, other classes of mycolic acids may be useful as antigens in the present invention. Suitable mycolic acid compounds may include an alkene functional group in place of the proximal cyclopropyl group shown on figures IIa, IIb, IIc and IId. Further suitable classes of mycolic acids include those substituted with epoxy and alkene groups in the meromycolate moiety, in place of the distal cyclopropyl, methoxy, hydroxyl or keto group. The proximal groups in such compounds may be cyclopropyl or alkene. The structure of such compounds will be known to the person skilled in the art. Thus each antigen used in the method of the present invention is preferably a mycolic acid-derived antigen which may be selected from keto mycolic acids, hydroxy mycolic acids, alpha mycolic acids, methoxy mycolic acids, epoxy mycolic acids and alkene mycolic acids.

Some analogues of mycolic acids suitable for use in preparing the antigens of the invention are wax esters: These compounds suitably have the formula (VI):

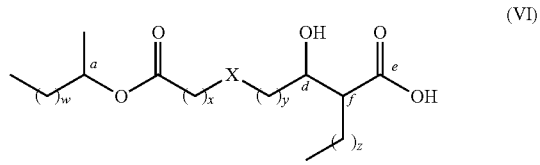

(VI)

wherein w is from 2 to 40, x is from 2 to 40, y is from 2 to 40, z is from 4 to 40 and X is a three carbon fragment including an alkane, alkene or cyclopropyl moiety.

Suitably X is a group of formula (VIa), (VIb), (VIc) or (VId):

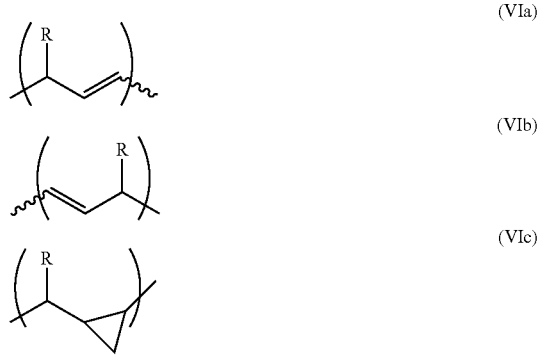

(VIa)

(VIb)

(VIc)

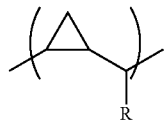

(VId)

wherein R is methyl or hydrogen. The double bond in formula (VIa) and (VIb) may be cis or trans.

In embodiments in which X is (VIa) or (VIb) and the double bond is trans, R is preferably methyl.

In embodiments in which the double bond is cis, R is preferably hydrogen.

The cyclopropyl group of fragment (VIc) or (VId) may be cis or trans.

In preferred embodiments in which X is (VIc) or (VId) R is preferably methyl.

In some especially preferred embodiments X is a fragment of formula (VIc) and the wax ester has the formula (VII):

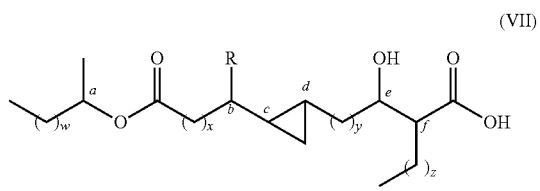

(VII)

Preferably w is from 10 to 32, preferably from 4 to 24; x is from 8 to 24, preferably from 12 to 18; y is from 10 to 32, preferably from 14 to 24; z is from 16 to 30; preferably from 22 to 26; and R is $C_1$ to $C_4$ alkyl, preferably methyl.

Other suitable analogues of mycolic acids for use in preparing the antigens of the present invention include long chain fatty acids of formula RCOOH wherein R is an alkyl or alkenyl group having 6 to 50 carbon atoms, preferably 12 to 40 carbon atoms. β-hydroxy acids are other preferred analogues.

Some further preferred compounds for use as antigens in the present invention are mixed mycolic acid esters of sugars and monohydric or polyhydric alcohols. In some embodiments the antigen may be a mixed sugar ester including a sugar moiety, the residue of a mycolic acid and the residue of a wax ester.

In some preferred embodiments the antigen is a synthetic antigen.

Suitably the antigen is at least 90% pure, for example at least 95% pure or at least 99% pure.

Preferably the antigen is a synthetic antigen which is at least 90%, preferably at least 95% or at least 99% pure.

By at least 90% pure we mean that at least 90% of the molecules of the antigen compound are identical i.e. the same homologue, the same stereoisomer and the same regioisomer.

In some embodiments a mixture of two or more antigens may be provided in the system, for example at one or more positions on a substrate. In preferred embodiments in which mixtures are present the structure of all compounds and preferably the relative amounts of each compound are known.

Preferred mixtures are mixtures of synthetically prepared antigens.

An advantage of using synthetically prepared antigens is that the compounds may be provided in high purity. Natural mycolic acid arabinose esters contain complex mixtures of different homologues which are very difficult to separate. The use of synthetic compounds allows single compounds or known mixtures to be used. This enables antigens having a high degree of specificity and/or sensitivity for a particular antibody or antibodies to be used.

In some embodiments the system may comprise an adjuvant compound which enhances the binding of the biomarker with the antigen. For example, when the system comprises a substrate which carries the antigen, the substrate may carry an adjuvant compound which enhances the binding of the biomarker with the antigen.

In some embodiments the system may comprise one or more further antigens. For example, when the system comprises a substrate which carries the antigen, the substrate may carry one or more further mycolic-acid derived antigens.

Each of the one or more further antigens is suitably selected from one or more of the following classes of compounds:
(i) mycolic acids obtained from natural sources;
(ii) synthetically prepared mycolic acids;
(iii) salts of mycolic acids;
(iv) esters of mycolic acids (i) and/or (ii);
(v) sulfur-containing mycolic acids and/or salts or esters thereof;
(vi) simple structural analogues of mycolic acids and/or salts or esters thereof;
(vii) mycolic acid wax esters or salts or derivatives thereof.

In some embodiments the substrate may carry two or more different antigens at different positions. The two or more antigens may each be arabinose ester derived antigens.

Alternatively the system may comprise one or more wax ester derived antigens and one or more further antigens selected from among classes (i) to (vi). For example, when the system comprises a substrate which carries the antigen, the substrate may carry one or more wax ester derived antigens and one or more further antigens selected from among classes (i) to (vi).

Mycolic acids obtained from natural sources (i) are typically available as mixtures. These typically contain different classes of mycolic acids and each class will usually contain a complex mixture of different homologues.

It is highly advantageous to use synthetically prepared mycolic acids (ii) since these are available as single compounds in high purity (for example greater than 95% or greater than 99%). The use of single compounds allows greater selectivity to be achieved.

Salts of natural mycolic acids and/or synthetic mycolic acids (iii) may be useful. Suitable salts include ammonium, alkali metal and alkaline earth metal salts, for example salts of lithium, potassium, sodium, calcium or barium.

Suitable esters (iv) for use as antigens include esters of simple monohydric and polyhydric alcohols and sugar esters. Suitably esters include glycerol esters of mycolic acids. Some particularly preferred antigens are sugar ester of mycolic acids. Some naturally occurring sugar esters of mycolic acids are trehalose monomycolates or trehalose dimycolates (also known as cord factors). Cord factors can be isolated as mixtures from natural sources. Esters of mycolic acids for use herein as antigens may be synthetically prepared. They may be prepared by esterification of synthetically prepared mycolic acids or by esterification of mycolic acids isolated from natural sources.

By sulfur-containing mycolic acids and/or esters or salts thereof (v) we mean to refer to synthetic compounds which are analogues of natural mycolic acid compounds rather than naturally occurring compounds that contain sulfur. Suitable sulfur-containing mycolic acid derivatives may include any compound in which one or more carbon atoms and/or one or more oxygen atoms of a mycolic acid derived compound has been replaced by a sulfur atom. Sulfur-containing mycolic acid derivatives also include compounds in which a hydrogen substituent has been replaced with a moiety "SX" wherein X is hydrogen, $SR^1$ or $COR^2$ in which $R^1$ is an optionally substituted alkyl, alkenyl, acyl or aryl group and $R^2$ is an optionally substituted alkyl, alkenyl or aryl group.

Simple structural analogues of mycolic acids and/or esters or salts thereof (vi) which may be used herein as antigens include compounds which include fewer functional groups and/or stereocentres than are found in natural mycolic acid compounds but have many structural features in common, for example they include a similar number of carbon atoms and have a simpler substitution pattern.

As described above, mycolic acid wax esters (vii) include a cyclopropyl or an alkene group and an internal ester group. These can be isolated from natural sources (typically as mixtures of homologues) or they can be prepared synthetically. Salts and esters of these wax esters thereof can also be used.

Synthetically prepared antigens are preferred as they can be prepared in high purity.

Some especially preferred further antigens for use in the present invention are trehalose esters of mycolic acids or analogues thereof. Suitable trehalose esters include trehalose monomycolates and trehalose dimycolates. Trehalose dimycolates (or cord factors) have the structure shown in formula V wherein MA represents the residue of a mycolic acid:

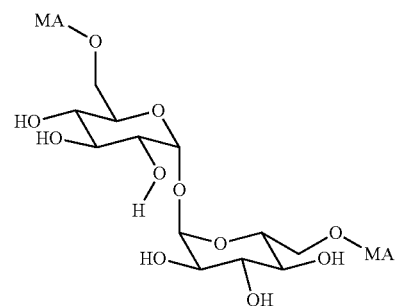

Formula V

In formula V each MA residue may be of the same or a different mycolic acid.

Step (a) may involve providing a substrate which carries the antigen.

Any suitable substrate may be used. For example the substrate may be a multiwell plate, typically made of polystyrene of the type commonly used in ELISA assays. Multiwell plates of this type are known to the person skilled in the art. In such embodiments the antigens are suitably immobilised on the substance by conventional means.

In some preferred embodiments the substrate is a porous substrate.

The porous substrate may be any material which allows another medium to pass through it. Suitably the porous substrate allows liquid compositions and semi-solid or viscous liquid compositions (for example gels and pastes) to pass through.

Any suitable porous substrate may be used. Suitably the porous substrate is a woven material. Preferably the porous substrate is a cellulosic material.

The porous material carries an antigen. The antigen may be carried within the porous material or on the surface of the porous surface.

Preferably the antigen forms a chemical interaction with the surface of the substrate. This may involve a polar interaction, for example dipole-dipole interactions or hydrogen bonding; or a non-polar interaction, for example Van der Waals forces.

In some preferred embodiments the antigen forms hydrogen bonds with functional groups at the surface of the substrate.

To prepare the substrate the antigen may be directly applied to the substrate.

In some preferred embodiments in which the substrate is a cellulosic material, a solution or suspension of the antigen may be applied to the substrate and the solvent allowed to evaporate. Without wishing to be bound by theory it is believed that hydrogen bonds form between the antigen and hydroxy groups of the cellulose.

Suitably the antigen is dissolved in a solvent. This may be an organic solvent, for example a mixture of hexanes; or an aqueous solvent, for example a buffer. The solution of antigen is suitably applied to the substrate and the solvent is then allowed to evaporate.

The antigen may be encapsulated, for example in a liposome.

Suitably a small spot of antigen is applied to the substrate at one or more positions.

Areas of the substrate which do not contain an antigen spot or spots may be "blocked", for example an impermeable coating may be applied to the surface of the substrate in these regions.

In step (b) of the method of the present invention the system is contacted with a sample obtained from the individual. For the avoidance of doubt the sample is collected from the individual prior to carrying out the method of the present invention which is an in vitro method.

Any suitable sample may be tested using the present invention. Suitably the sample is selected from serum, blood, saliva, urine or sputum. In some embodiments the sample is blood. It may be serum.

The sample may contain a biomarker which becomes bound to or interacts with the antigen.

The sample may be directly contacted with the system or it may be diluted, filtered or otherwise purified prior to contact with the system. Suitable diluents, filtration methods and purification techniques will be known to the person skilled in the art.

The sample is suitably contacted with the system as a liquid or semi-liquid composition.

Preferably it is a liquid composition.

In some embodiments the sample is diluted before contacting with the system. It may be diluted with an aqueous composition, suitably an aqueous buffer. Preferably it is diluted with an aqueous buffer having a pH of 6 to 8, preferably about 7. A casein buffer is especially preferred.

In some embodiments, wherein the system comprises a substrate which carries the antigen, the substrate may be immersed in the sample or a composition comprising the sample.

In some embodiments, wherein the system comprises a substrate which carries the antigen, the sample or a composition comprising the sample may be passed over the surface of the substrate.

In some embodiments, wherein the system comprises a substrate which carries the antigen, in which the substrate is a porous substrate, the sample or a composition comprising the sample is contacted with a surface of the substrate and allowed to pass through the substrate.

In such embodiments the substrate may suitably be a sheet material. The sample or a composition comprising the sample may pass from one edge of the substrate to the opposite edge or may be contacted with a face of the substrate and pass through the substrate to the opposite face.

The sample or a composition comprising the sample may be contacted with the entire area of the substrate or a portion of the substrate, suitably the portion which carries the antigen.

Step (c) of the method of the present invention involves detecting the presence or absence of the binding of a biomarker in the sample with the antigen.

Any suitable method may be used to detect the presence or absence of the binding of the biomarker.

In some preferred embodiments step (c) involves the steps:
  (i) contacting the system with a composition comprising a secondary antibody; and
  (ii) observing the system.

In some preferred embodiments wherein the system comprises a substrate which carries the antigen, step (c) may involve the steps:
  (i) contacting the substrate with a composition comprising a secondary antibody; and
  (ii) observing the substrate.

Suitably the composition comprising a secondary antibody comprises a carrier for the secondary antibody. The carrier is suitably a colorimetric substrate or is able to bind to a colorimetric substrate. The carrier for the secondary antibody may be selected from nanoparticles of a metal or nanoparticles of a polymeric material.

The composition comprising a secondary antibody may comprise a secondary antibody bound to an enzyme, for example an alkaline phosphatase. In such embodiments using a secondary antibody bound to an enzyme, a colorimetric substrate may then be used to enable binding of the antigen to an antibody in the sample to be detected/observed.

Step (c) may involve contacting the system, for example the substrate if present, with a composition comprising colloidal gold particles, wherein the colloidal gold particles carry a secondary antibody.

Any antibody or antibody conjugate which interacts with the biomarker may be used as the secondary antibody. Preferred secondary antibodies include Immunoglobulin G and Immunoglobulin M.

In some embodiments the secondary antibody is linked to an enzyme via bio conjugation. Such secondary antibodies are well known to the person skilled in the art and are commonly used in ELISA assays.

In some preferred embodiments step (c) involves contacting the substrate with a composition comprising colloidal gold particles wherein the colloidal gold particles carry a secondary antibody.

The composition comprising colloidal gold particles is preferably an aqueous suspension of gold nanoparticles.

Suitably the nanoparticles have an average size of from 1 to 200 nm, preferably from 5 to 150 nm, suitably from 10 to 100 nm, suitably from 20 to 80 nm, for example about 40 nm.

The composition may comprise one or more further ingredients for example cosolvents, preservatives, or buffering agents.

Preferably the composition comprises a buffer. Preferably the composition has a pH of from 5 to 9, preferably from 6 to 8, for example about 7. In some especially preferred embodiments the composition comprises a casein buffer.

Suitably the nanoparticles of gold carry a secondary antibody on their surface.

The antibody suitably forms an interaction with the surface of the gold nanoparticles.

In some preferred embodiments the gold nanoparticles are coated with a composition which promotes interaction with the secondary antibody. Preferably the gold particles are coated with a polymer. Suitable polymers are able to stabilize the gold particles and covalently bind antibodies.

Suitably there is one or more washing step between step (c) (i) and step (c) (ii).

After the substrate is contacted with a composition comprising colloidal gold particles, the substrate is suitably washed. Preferably it is washed with a composition comprising a buffer. Preferably it is washed with a composition of pH 6 to 8, suitably about 7. An aqueous composition comprising a casein buffer is especially preferred.

Step (c) (ii) involves observing the substrate.

Suitably in embodiments in which the biomarker is present in the sample a colour change in the region of the substrate which carries the antigen is observed. If the biomarker is absent no colour change is observed.

Thus in preferred embodiments a positive sample in which a biomarker has bound with a particular antigen causes a colour change and a negative sample in which there is no binding causes no colour change.

In some embodiments step (ii) may involve quantitatively measuring the colour change. Quantitative analysis of this type may also help determine the severity of infection with a mycobacterial disease.

Step (ii) may also involve measuring a response change, for example a colour change, over time. This information may also be useful in determining the type or extent of infection with a mycobacterial disease.

However in preferred embodiments step (ii) may involve simply visually observing the presence or absence of a colour change to provide a qualitative assessment.

In the method of the present invention when the sample is contacted with the substrate in step (b), if the biomarker is present it interacts with the antigen carried on the substrate and is thus "tethered" to the surface of the substrate.

If no biomarker is present no interaction occurs with the antigen and the biomarker is not present at the surface of the substrate.

In step (c) (i) the substrate may be contacted with the composition comprising colloidal gold particles which carry a secondary antibody or an enzyme-linked secondary antibody. If following step (b) the biomarker is carried on the surface of the substrate the secondary antibody interacts with the biomarker and tethers the gold particles to the substrate. If no biomarker is carried on the surface of the substrate then the secondary antibody and appendent gold particles or enzyme pass through the substrate.

The gold particles have a red colour. Thus when a biomarker is present the region of the substrate which carries the antigen is red at the end of step (c) (i). If no biomarker is present no colouration of the substrate is observed.

When the secondary antibody is linked to an enzyme in the manner of an ELISA assay the method may suitably include a step of adding a composition comprising a colorimetric substrate. The colorimetric substrate suitably undergoes a colour change upon reaction with the enzyme indicating the presence of the enzyme and thus the secondary antibody and the biomarker. Suitable enzyme compositions are commonly used in ELISA assays and will be known to the person skilled in the art.

A particular advantage of the present invention is that it enables a very quick, simple test to be carried out to determine whether or not a particular sample contains a biomarker. Suitably it is used to determine whether or not the sample contains a biomarker indicative of exposure to mycobacteria, for example an antibody indicative of infection with or exposure to a mycobacterial disease. The method of the present invention may be carried out at remote locations, for example where there is no or limited access to hospitals, clinics, laboratories or specialist services. The colour change provides an immediate or almost immediate indication of whether the provider of the sample is infected with a mycobacterial disease.

The method of the present invention may be carried out using traditional ELISA methodology. Such methods are well known to the person skilled in the art and commonly known variations are within the scope of the invention.

The present invention may thus provide the use of a mycolic acid arabinose ester derived antigen in an ELISA assay to determine whether an individual is infected with a mycobacterial disease. Preferred features of this use are as defined in relation to the method of the first aspect.

In some preferred embodiments the method of the first aspect of the present invention comprises the steps of:
  (a) providing a porous substrate which carries a mycolic acid arabinose ester derived antigen;
  (b) contacting the substrate with the sample; and
  (c) (i) contacting the substrate with a composition comprising colloidal gold particles; wherein the colloidal gold particles carry a secondary antibody; and
    (ii) observing the substrate.

Preferred features of this preferred method are as previously defined herein.

Suitably the porous substrate is a cellulosic substrate. Suitably the composition comprising colloidal gold particles is an aqueous suspension of gold nanoparticles.

In especially preferred embodiments of the present invention the system comprises at least two different mycolic-acid derived antigens. At least one of the mycolic acid derived antigens is an arabinose ester. The other antigens may be selected from any of the types of compounds previously described herein. Suitably the different antigens are each located at different positions on a substrate.

The diagnosis of mycobacterial diseases is known to be very difficult.

The present inventors have found that when the system comprises two or more different antigens, considering the observations related to these antigens in combination can lead to a higher accuracy in diagnosis of a disease. Thus the method may allow the interaction with multiple antigens to be measured simultaneously. In such embodiments step (c) involves detecting the presence or absence of the binding of a biomarker with each antigen separately.

By measuring the interaction with more than one antigen the present invention allows a greater degree of sensitivity and specificity to be achieved.

The inventors have surprisingly found that using a combination of different mycolic acid derived antigens allows a much more accurate and reliable diagnosis. These results can also be achieved quickly and cheaply.

Suitably in the method of the present invention the presence or absence of a colour change at two or more different positions on a substrate in combination leads to the determination of whether or not an individual is infected with a mycobacterial disease.

In preferred embodiments the one or more further antigens are selected from wax esters, free mycolic acids and sugar esters of mycolic acids.

In some embodiments the system comprises more than two mycolic-acid derived antigens, suitably at different positions. It may suitably comprise at least 3 different mycolic acid derived antigens, suitably at different positions, for example at least 4, at least 5 or at least 6.

In some especially preferred embodiments the system comprises from 5 to 8 different antigens. Preferably each of these antigens is synthetically prepared. Preferably each is at least 90% pure, preferably at least 95% pure, for example at least 99% pure. The use of a combination of a number of different responses to antigens allows a higher degree of sensitivity and specificity to be achieved and enables distinction between different mycobacterial diseases.

According to a second aspect of the present invention there is provided a kit for determining the presence or absence of a biomarker in a sample, the kit comprising:
(x) a system which comprises an antigen which is an arabinose ester of a mycolic-acid or an analogue thereof; and
(y) a composition comprising a secondary antibody.

Suitably the second aspect of the present invention provides a kit for determining the presence or absence of a biomarker in a sample, the kit comprising:
(x) a substrate which carries an antigen which is an arabinose ester of a mycolic-acid or an analogue thereof; and
(y) a composition comprising a secondary antibody.

Preferred features of the second aspect are as defined in relation to the first aspect and features described in relation to the second aspect may also apply to the first aspect. As described above the substrate may be a multiwell plate as commonly used in an ELISA assay and the composition comprising a secondary antibody may comprise an enzyme linked secondary antibody. In such embodiments the kit may further comprise a composition comprising a substrate for the enzyme. As will be understood by the skilled person the substrate for the enzyme is a molecule with which the enzyme reacts and is distinct from the substrate previously defined herein which is a carrier for the antigens. The substrate for the enzyme may be a colorimetric substrate.

As previously described herein, in some preferred embodiments the substrate is a porous material, preferably a porous sheet material, for example a cellulosic material. In such embodiments the composition comprising the secondary antibody may be a composition comprising particles of colloidal gold wherein the colloidal gold particles carry the secondary antibody on their surface.

In the kit of the second aspect the substrate is preferably located within a suitable housing.

Preferably the substrate is positioned within the housing so as to enable the sample to contact the substrate.

Suitably the housing includes an aperture to enable the sample to contact the substrate in the region which carries the antigen.

In some preferred embodiments in which the substrate is porous it is positioned within the housing to enable the sample to pass through from one side of the substrate to the other.

The housing may further comprise a chamber to collect the sample and other compositions after they pass through the substrate. The chamber may include an absorbent material to soak up the excess sample, excess secondary antibody composition and/or any washing compositions.

The housing may be made from any suitable material. Preferably it is a plastic housing.

The absorbent material is preferably a sponge-like material.

According to a third aspect of the present invention there is provided a device comprising a housing and a system; wherein the system comprises an antigen which is an arabinose ester of a mycolic acid or an analogue thereof.

Suitably this third aspect of the present invention provides a device comprising a housing and a substrate; wherein the substrate carries the antigen which is an arabinose ester of a mycolic acid or an analogue thereof.

Preferred features of the device of the third aspect are as defined in relation to the first and second aspects. The kit of the second aspect preferably comprises a device of the third aspect and a composition comprising a secondary antibody.

When used to analyse known samples of sera from cattle some of whom had been infected with Johne's disease, the method of the present invention was found to provide a faster and more accurate method of discrimination between positive and negative samples compared with using standard methods of the prior art. The method of the present invention is also more suitable for point of care use than prior art methods, for example in environments with limited access to laboratories.

Embodiments of the invention which use a porous substrate and a secondary antibody, for example carried on colloidal gold particles, are particularly suitable for use in remote locations.

When the present invention is used to test for disease antibodies indicative of infection with a mycobacterial disease, for example Johne's disease, it can provide results very quickly, with good accuracy and at relatively low cost. It therefore provides significant advantages over the prior art.

A fourth aspect of the present invention provides a composition comprising at least 90 wt % of a single compound of formula (III):

$$(M)_x\text{-}(S)_y\text{-}(M')_z \qquad \text{(III)}$$

wherein x is from 1 to 6, y is from 1 to 12, z is from 0 to 10, each M and each M' is independently a mycolic acid moiety including a β-hydroxy acid moiety and each S is a monosaccharide unit, provided that at least one S is an arabinose unit.

The compound of formula (III) is as defined in relation to the first aspect.

The composition of the fourth aspect comprises at least 90 wt % of a single compound of formula (III). Suitably the single compound is a single homologue, single stereoisomer and single regioisomer. Suitably the composition of the fourth aspect comprises at least 95 wt % of a single compound, preferably at least 97 wt %, more preferably at least 99 wt %.

The provision of highly purified single compounds is advantageous as the different compounds interact with different antibodies and thus elicit different immune responses. As such these single compounds can be used in therapeutic applications. They can also be used as adjuvants in vaccination.

Suitably the invention provides a composition of the fourth aspect for use in treatment of a disease of the immune system.

The present invention may thus provide compositions for the treatment of diseases of the immune system, in particular the immune system of mammals and especially humans.

Suitably the disease treated is a disease involving an out of control immune response or pathology causing immune response, for example an allergic immune disease or an autoimmune disease.

Preferably the compounds of the present invention are useful in the treatment of a disease in which Th2-lymphocyte activity contributes to the immune disease.

Examples of diseases which may be treated according to the present invention include asthma, rhinitis, hay fever, eczema and other allergic diseases; and autoimmune diseases, for example, systemic lupus erythematosus, Goodpasture's syndrome, Grave's disease, Myasthenia Gravis, type I diabetes and multiple sclerosis.

In preferred embodiments, the present invention is useful in the treatment of asthma and other allergic diseases. Allergic diseases are known to the person skilled in the art and include, but are not limited to, allergic asthma, allergic rhinitis, allergic conjunctivitis, eczema, airway hyperactivity, eosinophilic airway inflammation and atopic dermititis.

Suitably the invention may provide a composition of the fourth aspect for use as an adjuvant in vaccination.

The invention may further comprise a vaccine composition comprising a composition of the fourth aspect and a further antigen.

It is believed that particular compounds of formula III may be selected to control the immune response achieved in vaccination. For example some compounds may be particularly effective adjuvants for use in vaccination against extracellular antigens, for example viruses and extracellular bacteria. Such compounds may then preferentially elicit Th17 and Th1 lymphocyte responses and immune defences supported by these T-cell subsets. Other compounds may be particularly effective adjuvants for use in vaccination against intracellular antigens, for example mycobacteria, listeria and cancer. Such compounds may then preferentially elicit Th1 and cytotoxic T-lymphocyte responses and immune defences supported by these T-cell subsets.

In some alternative embodiments the compound of formula III may be selected such that when used as an adjuvant a humoral immune response is elicited that is supported by Th2 lymphocytes and provides protection against among other parasitic infections.

In some embodiments the composition of the fourth aspect comprises at least 90 wt % of a single compound selected from compounds having the formula A, B, C, D, E, F, G, H or I:

A.

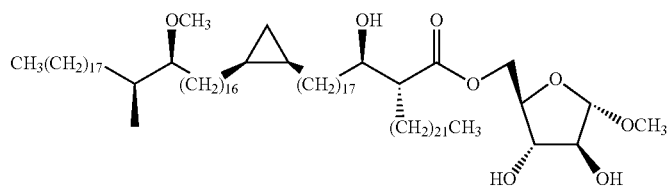

B.

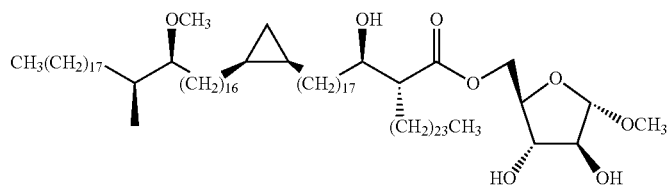

C.

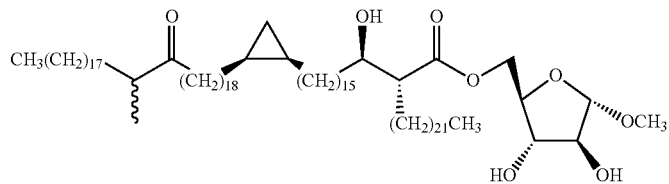

D.

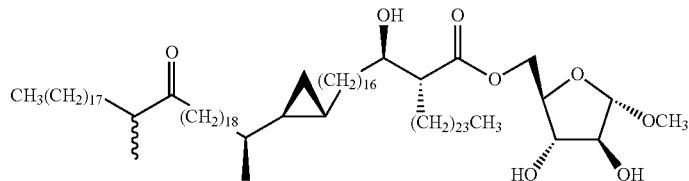

E.

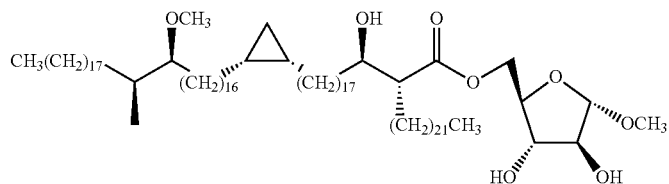

F.
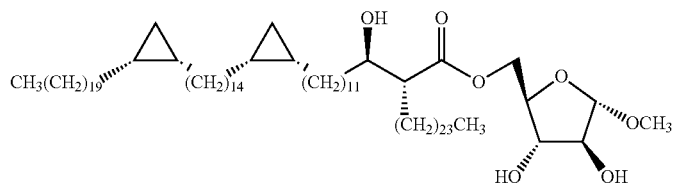
G.
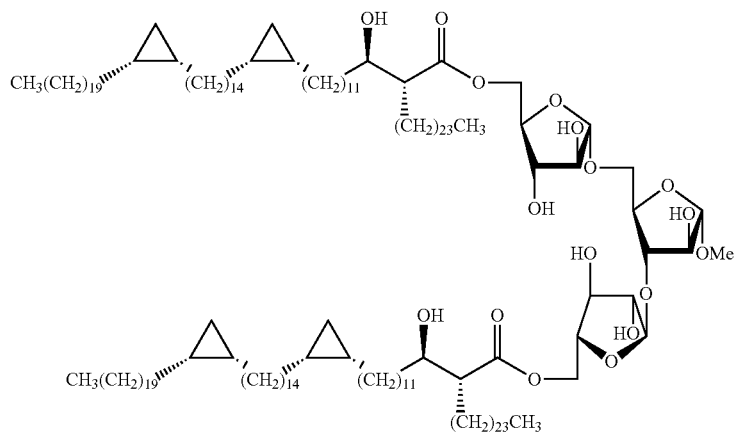
H.
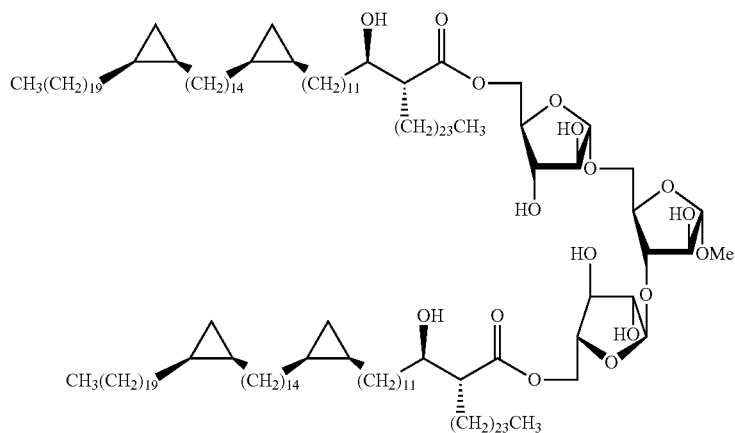
I.
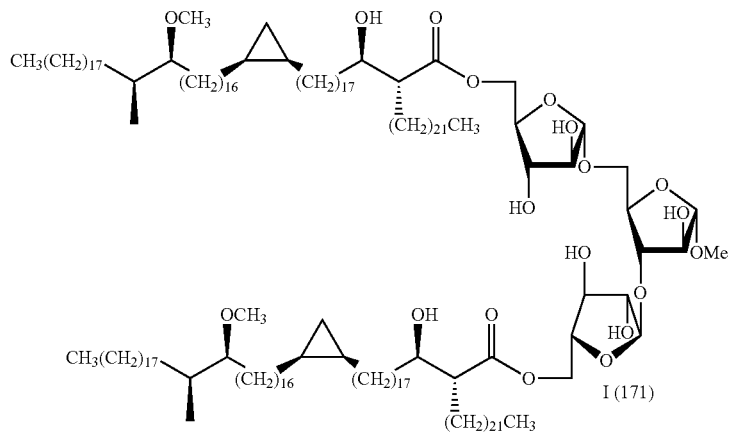
I (171)

In some embodiments the composition of the fourth aspect comprises at least 90 wt % of a single compound selected from compounds having the formula A, B, C, D, E, F or G:
A.
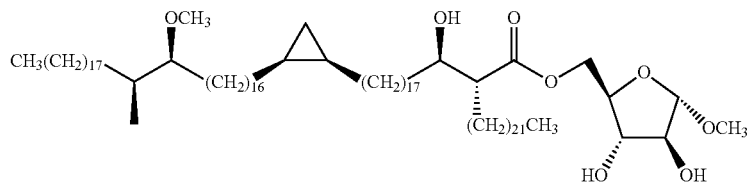
B.
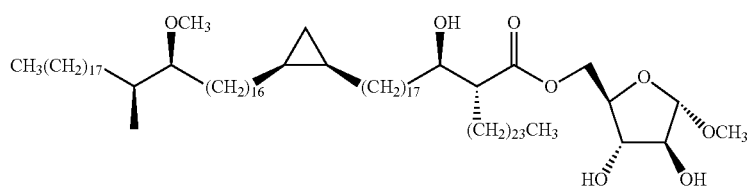
C.
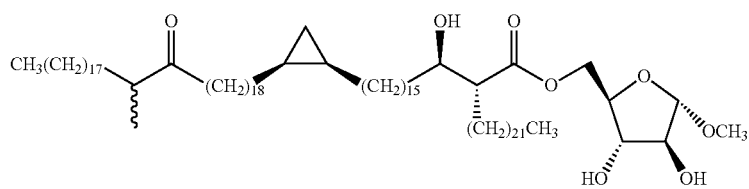
D.
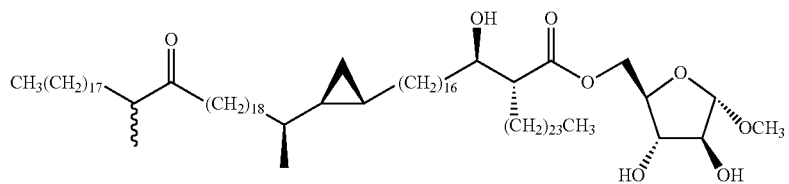
E.
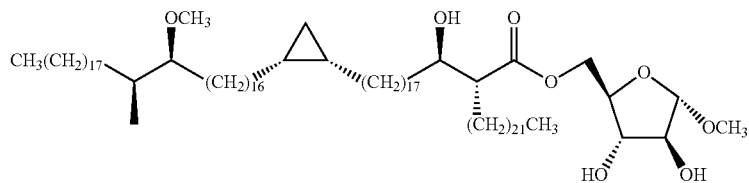
F.
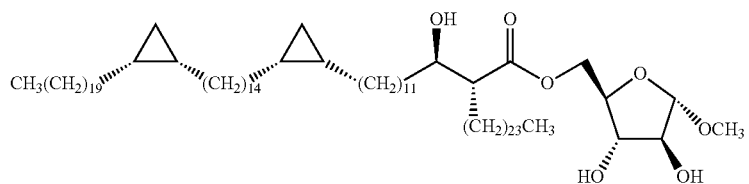

G.

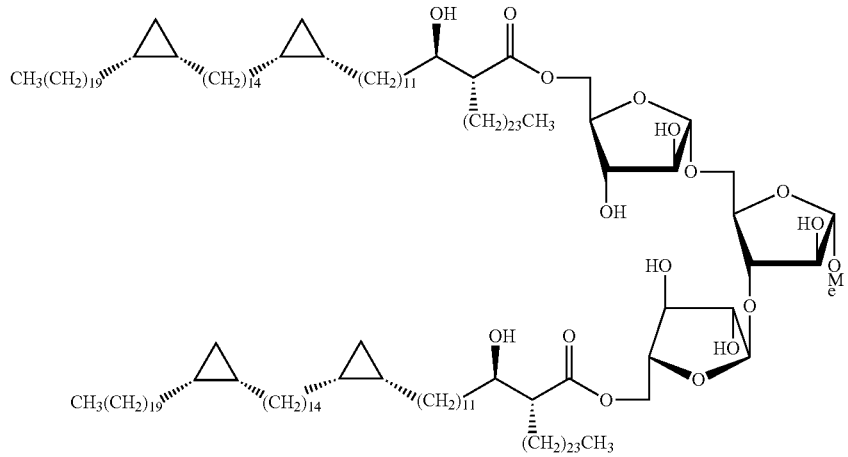

The invention will now be further described with reference to the following non-limiting examples:

Example 1: ELISA Test Method

ELISA assays were carried out as known to those practiced in the art using 96 well plates. In the first procedure, the ELISA assay was carried out on 96-well microplates and the purified antigens were dissolved in n-hexane at a concentration of 62.5 μg/mL. The antigen solution was diluted and 50 μL was placed in each well. The plates were left to dry at room temperature overnight. Blocking was done with 0.5% casein/PBS (400 μL/well) and the plates were left to incubate at 25° C. for 1 h. The casein was aspirated using the LT-3500 plate washer and the plates flicked dry. Then the serum (1:20 dilution in 0.5% casein/PBS, pH 7.4) was added to the plate (50 μL/well) and left to incubate at 25° C. for 1 h. The serum was aspirated and washed three times with (casein/PBS, 400 μL/well) using the same plate washer and the plates were flicked dry again. After that, the secondary antibody, in the example given IgG Fc (1:1000 dilution in 0.5% casein/PBS) was added to the plate (50 μL/well) and the plates were left to incubate at 25° C. for 30 min. The plates were washed three times again with casein/PBS (400 μL/well) and dried. Then, the OPD substrate was added to the plates, which were left to incubate at 25° C. for 30 min. Finally, 2.5 M $H_2SO_4$ (50 μL/well) was added and the absorbances of each well were read at 492, 450 and 630 nm using an LT-4000 plate reader.

Human serum used in this work was from the WHO sample bank. In this case, all the patients had presented at a hospital with the symptoms of TB. Clinical diagnosis was made on the basis of a series of standard assays.

All measurements were taken as four replicates unless otherwise stated. These were averaged to provide the data in the tables which are for the value at 492 nm.

Example 2: General Method for the Preparation of Arabinose Mycolate Antigens Tosylate 5 (Scheme 2), prepared by known procedures, was reacted with the chosen simple fatty acid or mycolic acid RCOOH (Scheme 1, where the chosen R groups are indicated by formula d-i, respectively) by alkylative esterification with cesium hydrogen carbonate in dry DMF:THF at 70° C. to give the compounds 6d-i (Scheme 2, where compounds 6d-i contain respective R groups of formula d-i); these were then debenzylated by hydrogenolysis in dry $CH_2Cl_2$:MeOH (1:1) in the presence of $Pd(OH)_2$ under a hydrogen atmosphere to give compounds 7d-i (Scheme 2, where compounds 7d-i contain respective R groups of formula d-i). Firstly condensation of methoxy-cis-cyclopropane mycolic acid which is present in *Mycobacterium kansasii*, led to compound 6d which on hydrogenolysis gave compound 7d. Then alkylative esterification of methoxy-cis-cyclopropane mycolic acid which is present in *M. tuberculosis* gave compound 6e which on hydrogenolysis led to compound 7e. The same procedure was repeated using the other single synthetic mycolic acids shown.

Scheme 1: Examples of mycolic fragments (mycolic acid = RCOOH)

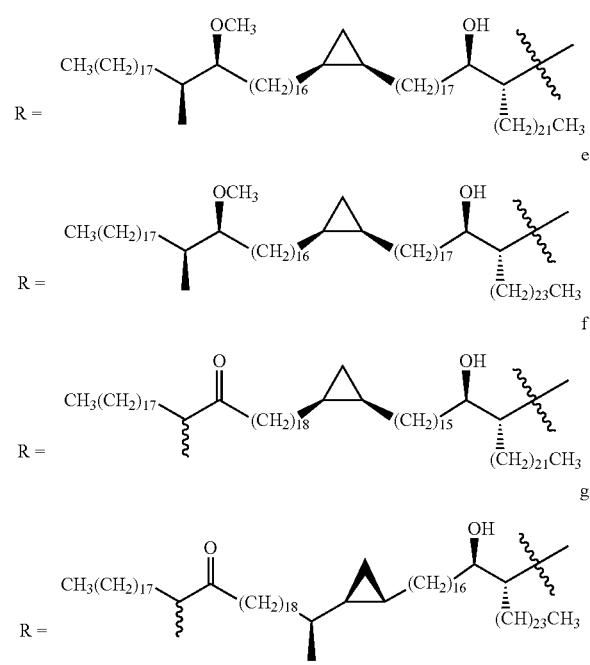

-continued

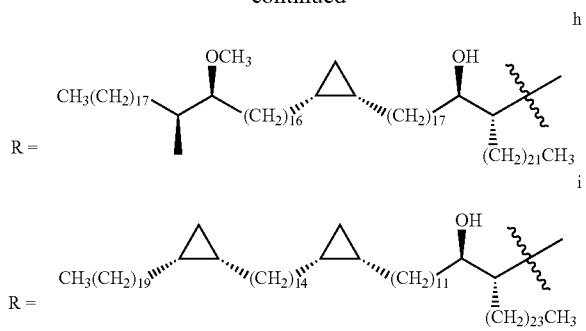

Scheme 2: preparation of arabinose mycolate antigens

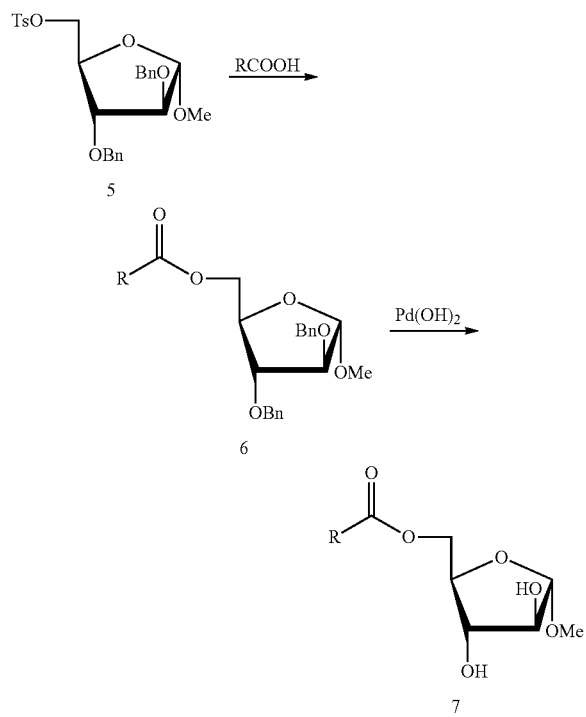

TABLE 1

Yields of products 6 and 7

| R | 6 (%) | 7 (%) |
|---|-------|-------|
| d | 75%   | 65%   |
| e | 80%   | 76%   |
| f | 80%   | 63%   |
| g | 92%   | 80%   |
| h | 77%   | 79%   |
| i | 87%   | 80%   |

Example 3: preparation of Methyl 5-O-(2-[(R)-1-hydroxy-18-[(1R,2S)-2-[(17S,18S)-17-methoxy-18-methylhexatri acontyl]cyclopropyl]-octadecyl]tetracosanoate) α-D-arabinofuranoside (7d)

Cesium hydrogen carbonate (0.098 g, 0.505 mmol) was added to a stirred solution of tosylate (0.0546 g, 0.1000 mmol) (Ishiwata, A., Akao, H., Ito, Y., Sunagawa, M., Kusunose, N. & Kashiwazaki, Y. 2006, "Synthesis and TNF-α inducing activities of mycoloyl-arabinan motif of mycobacterial cell wall components", Bioorganic & medicinal chemistry, vol. 14, no. 9, pp. 3049-3061) and 2-[(1R)-1-hydroxy-18-[2-(17-methoxy-18-methylhexatriacontyl)cyclo propyl]octadecyl] tetracosanoic acid (0.100 g, 0.081 mmol) in dry DMF:THF (1:5, 2 ml) at room temperature and the reaction mixture was stirred at 70° C. for two days. The suspension was diluted with ethyl acetate (10 ml) and water (10 ml). The organic layer was separated and the aqueous layer was re-extracted with ethyl acetate (2×10 ml). The combined organic layers were washed with water (15 ml) and brine (15 ml). The organic layer was dried, filtered and evaporated to give a thick oil residue. The residue was purified by column chromatography on silica eluting with hexane/ethyl acetate (10:1) to a colourless thick oil compound 6d (0.0949 g, 75%), [Found (M+Na)$^+$: 1574.452, $C_{103}H_{186}NaO_8$, requires: 1574.4045]; $[\alpha]_D^{23}$=+18 (c 0.1, $CHCl_3$), which showed $\delta_H$ (500 MHz, $CDCl_3$): 7.38-7.29 (10H, m), 4.92 (1H, s), 4.58 (1H, d, J 12 Hz), 4.56 (1H, d, J 12 Hz), 4.51 (1H, d, J 12 Hz), 4.48 (1H, d, J 12 Hz), 4.31-4.28 (2H, m), 4.24-4.20 (1H, m), 3.99 (1H, dd, J 2.7, 0.9 Hz), 3.84 (1H, dd, J 6.4, 2.6 Hz), 3.66-3.60 (1H, m), 3.38 (3H, s), 3.35 (3H, s), 3.00-2.93 (1H, m), 2.52 (1H, br.s), 2.43 (1H, dt, J 9.1, 5.5 Hz), 1.72-1.61 (2H, m), 1.60-1.07 (141H, m), 0.89 (6H, t, J 6.9 Hz), 0.86 (3H, d, J 6.8 Hz), 0.69-0.62 (2H, m), 0.57 (1H, td, J 8.4, 4.1 Hz), −0.32 (1H, q, J 5.2 Hz); $\delta_C$ (101 MHz, $CDCl_3$): 175.0, 137.5, 137.3, 128.6, 128.5, 127.9, 127.8, 107.2, 87.9, 85.4, 83.7, 79.4, 77.0, 72.4, 72.2, 72.1, 63.5, 57.7, 54.9, 51.5, 35.5, 35.3, 32.5, 32.3, 31.9, 31.3, 31.0, 30.9, 30.8, 30.79, 30.6, 30.58, 30.5, 30.47, 30.4, 30.38, 30.37, 30.3, 30.29, 30.2, 30.19, 30.1, 29.9, 29.8, 29.7, 29.6, 29.5, 29.4, 29.3, 29.2, 29.18, 29.17, 29.16, 29.15, 29.0, 28.9, 28.8, 28.7, 28.5, 28.4, 28.3, 27.6, 27.4, 27.3, 26.9, 26.1, 25.7, 22.6, 15.7, 14.8, 14.1, 10.9; vmax: 3479, 3064, 2923, 2853, 1733, 1465, 1100, 721 cm$^{-1}$.

Palladium hydroxide on activated charcoal (20% Pd(OH)$_2$ —C, 0.003 g, 0.15 fold by weight) was added to a stirred solution of compound 6d (0.020 g, 0.012 mmol) in dry $CH_2Cl_2$:MeOH (1:1, 2 ml) at room temperature under hydrogen atmosphere. The reaction mixture was stirred overnight then TLC showed no starting material was left. The mixture was filtered off and the solvent was evaporated to give a residue which was purified by column chromatography on silica eluting with hexane/ethyl acetate (1:1) to give a colorless oil compound 7d (0.011 g, 65%), [Found (M+Na)$^+$: 1394.266, $C_{89}H_{174}NaO_8$, requires: 1394.3106]; $[\alpha]_D^{23}$=+10 (c 0.7, $CHCl_3$); $\delta_H$ (400 MHz, $CDCl_3$): 4.89 (1H, s), 4.50 (1H, dd, J 12, 3.8 Hz), 4.32 (1H, dd, J 12, 4.4 Hz), 4.20-4.16 (1H, m), 4.07 (1H, d, J 5.6 Hz), 4.00-3.96 (1H, m), 3.74-3.64 (1H, m), 3.41 (3H, s), 3.35 (3H, s), 3.00-2.93 (1H, m), 2.70-2.57 (2H, m), 2.47-2.43 (1H, m), 2.36-2.26 (1H, m), 1.59-1.19 (143H, m), 0.89 (6H, t, J 6.8), 0.86 (3H, d, J 6.9 Hz), 0.69-0.63 (2H, m), 0.60-0.53 (1H, m), −0.32 (1H, dd, J 9.6, 4.5 Hz); $\delta_C$ (101 MHz, $CDCl_3$): 174.9, 108.7, 85.4, 83.8, 80.4, 78.4, 77.3, 77.0, 76.6, 72.8, 63.2, 57.7, 55.0, 52.2, 35.3, 35.2, 32.3, 31.9, 30.5, 30.2, 30.0, 29.9, 29.7, 29.68, 29.6, 29.5, 29.4, 29.3, 28.7, 27.5, 27.4, 26.1, 25.4, 22.7, 15.7, 14.99, 14.1, 10.9; vmax: br. 3436, 2918, 2850, 1732, 1467, 1099, 720 cm$^{-1}$.

Example 4

The following antigens were prepared using the method of example (2 or 3) or an analogous method.

A.
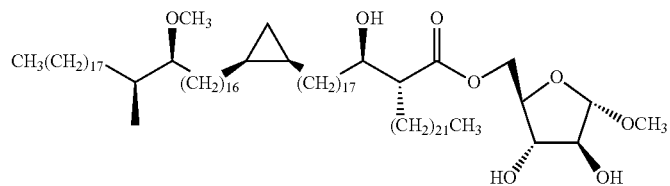
B.
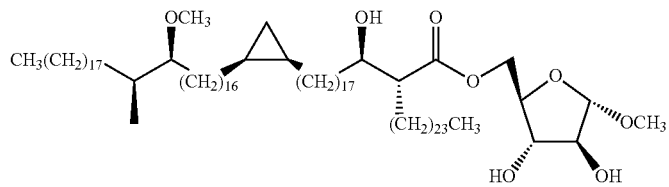
C.
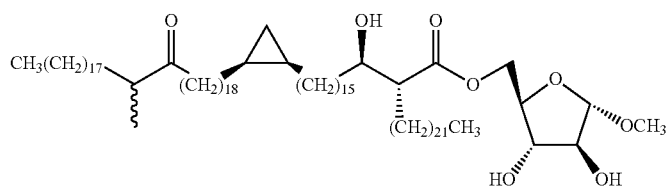
D.
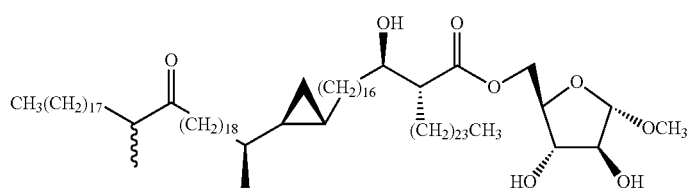
E.
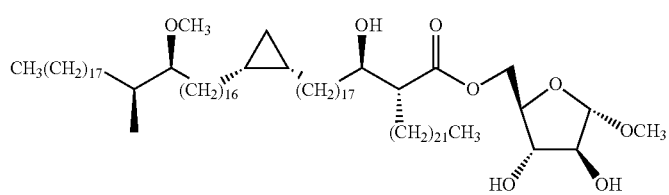
F.
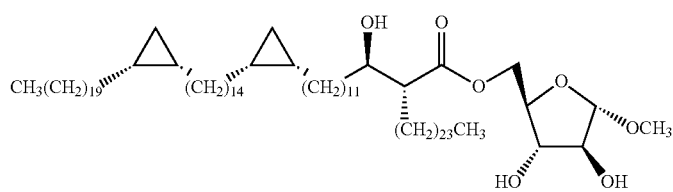

-continued

G.

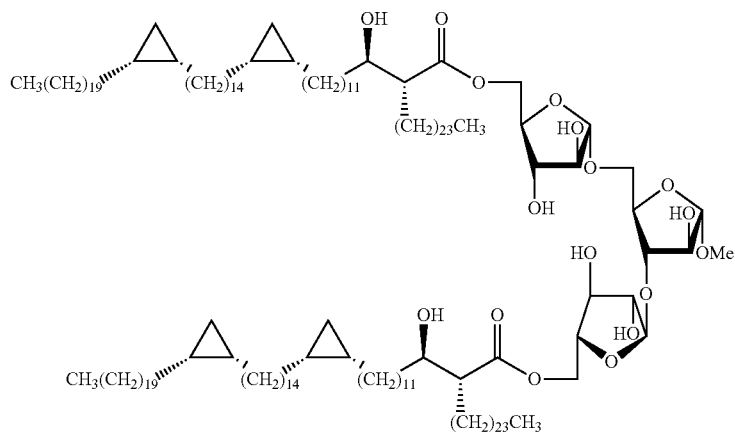

Example 5

64 serum samples from patients with symptoms of tuberculosis, and taken from individuals in high burden TB populations, clinically diagnosed as positive (TB+) or negative (TB−) for infection with tuberculosis were tested according to the method of the present invention using antigens A to F of Example 4.

By selecting appropriate cut offs for a positive response, the antigens gave 100% sensitivity and the specificity shown in Table 2. Thus each different arabinose ester differentiates TB+ from TB− serum samples to a different extent depending on the mycolic acid structure.

All TB+ were culture positive, all TB− were culture negative.

The results are shown in Table 2.

TABLE 2

| | Antigens | | | | | |
|---|---|---|---|---|---|---|
| | A | B | C | D | E | F |
| 1 TB+ | 0.28* | 0.48* | 0.33* | 0.41* | 0.42* | 0.74* |
| 2 TB+ | 0.29* | 0.54* | 0.26* | 0.30* | 0.36* | 0.76* |
| 3 TB+ | 0.30* | 1.10* | 0.44* | 0.36* | 0.77* | 0.99* |
| 4 TB+ | 0.50* | 1.00* | 0.48* | 0.44* | 0.90* | 0.97* |
| 5 TB+ | 0.28* | 0.45* | 0.40* | 0.29* | 0.38* | 0.99* |
| 6 TB+ | 0.28* | 0.97* | 0.39* | 0.41* | 0.54* | 1.39* |
| 7 TB+ | 0.93* | 0.87* | 1.37* | 1.03* | 1.15* | 1.97* |
| 8 TB+ | 0.47* | 0.97* | 0.46* | 0.64* | 0.69* | 1.67* |
| 9 TB+ | 0.29* | 0.62* | 0.35* | 0.42* | 0.56* | 1.09* |
| 10 TB− | 0.21 | 0.56* | 0.22 | 0.26* | 0.35 | 0.59 |
| 11 TB− | 0.20 | 0.64* | 0.20 | 0.27* | 0.45* | 0.92* |
| 12 TB− | 0.18 | 0.44 | 0.18 | 0.18 | 0.29 | 0.84* |
| 13 TB− | 0.22 | 0.56* | 0.24 | 0.20 | 0.34 | 0.60 |
| 14 TB− | 0.49* | 0.91* | 0.56* | 0.60* | 0.58* | 1.30* |
| 15 TB− | 0.23 | 0.53* | 0.22 | 0.25 | 0.37* | 0.64 |
| 16 TB− | 0.31* | 0.52* | 0.30* | 0.32* | 0.42* | 0.56 |
| 17 TB− | 0.52* | 0.87* | 0.57* | 0.39* | 0.47* | 0.81* |
| 18 TB− | 0.28* | 0.44 | 0.32* | 0.28* | 0.25 | 0.68 |
| 19 TB− | 0.20 | 0.53* | 0.20 | 0.14 | 0.31 | 0.71* |
| 20 TB− | 0.34* | 0.63* | 0.41* | 0.23 | 0.38* | 1.03* |
| 21 TB− | 0.47* | 0.42 | 0.41* | 0.41* | 0.35 | 0.61 |
| 22 TB− | 0.23 | 0.33 | 0.31* | 0.28* | 0.24 | 0.66 |
| 23 TB− | 0.25 | 0.48* | 0.27* | 0.42* | 0.35* | 0.81* |
| 24 TB− | 0.29* | 0.81* | 0.53* | 0.39* | 0.26 | 0.62 |
| 25 TB− | 0.18 | 0.23 | 0.24 | 0.25* | 0.18 | 0.21 |
| 26 TB− | 0.52* | 0.64* | 0.90* | 0.66* | 0.24 | 0.72 |
| 27 TB− | 0.31* | 0.60* | 0.46* | 0.43* | 0.33 | 0.61 |
| 28 TB− | 0.28* | 0.42 | 0.42* | 0.38* | 0.23 | 0.38 |
| 29 TB− | 0.28* | 0.39 | 0.38* | 0.34* | 0.29 | 0.41 |
| 30 TB− | 0.32* | 0.41 | 0.39* | 0.31* | 0.24 | 0.39 |
| 31 TB− | 0.31* | 0.37 | 0.51* | 0.42* | 0.30 | 0.51 |
| 32 TB− | 0.34* | 0.68* | 1.01* | 1.09* | 0.57* | 0.91* |
| 33 TB− | 0.18 | 0.36 | 0.33* | 0.28* | 0.46* | 0.42 |
| 34 TB− | 0.39* | 0.47* | 0.52* | 0.46* | 0.51* | 0.49 |
| 35 TB− | 0.23 | 0.38 | 0.55* | 0.38* | 0.26 | 0.38 |
| 36 TB− | 0.11 | 0.28 | 0.25 | 0.17 | 0.23 | 0.28 |
| 37 TB− | 0.28* | 0.40 | 0.43* | 0.22 | 0.41* | 0.55 |
| 38 TB− | 0.29* | 0.44 | 0.43* | 0.36* | 0.40* | 0.52 |
| 39 TB− | 0.21 | 0.31 | 0.34* | 0.38* | 0.31 | 0.35 |

TABLE 2-continued

| | Antigens | | | | | |
|---|---|---|---|---|---|---|
| | A | B | C | D | E | F |
| 40 TB− | 0.18 | 0.28 | 0.26* | 0.25* | 0.25 | 0.35 |
| 41 TB− | 0.18 | 0.51* | 0.44* | 0.40* | 0.33 | 0.66 |
| 42 TB− | 0.30* | 0.49* | 0.42* | 0.42* | 0.42* | 0.55 |
| 43 TB− | 0.25 | 0.28 | 0.32* | 0.26* | 0.29 | 0.30 |
| 44 TB− | 0.41* | 0.60* | 1.32* | 1.19* | 0.67* | 0.98* |
| 45 TB− | 0.33* | 0.34 | 0.49* | 0.44* | 0.35* | 0.43 |
| 46 TB− | 0.13 | 0.27 | 0.28* | 0.13 | 0.26 | 0.31 |
| 47 TB− | 0.34* | 0.35 | 0.56* | 0.59* | 0.41* | 0.56 |
| 48 TB− | 0.32* | 0.29 | 0.55* | 0.31* | 0.17 | 0.32 |
| 49 TB− | 0.38* | 0.47* | 0.79* | 0.49* | 0.25 | 0.51 |
| 50 TB− | 0.35* | 0.31 | 0.38* | 0.32* | 0.30 | 0.37 |
| 51 TB− | 0.11 | 0.22 | 0.18 | 0.24 | 0.18 | 0.21 |
| 52 TB− | 0.21 | 0.28 | 0.32* | 0.30* | 0.26 | 0.36 |
| 53 TB− | 0.16 | 0.24 | 0.21 | 0.24 | 0.25 | 0.26 |
| 54 TB− | 0.17 | 0.25 | 0.26* | 0.26* | 0.20 | 0.27 |
| 55 TB− | 0.24 | 0.27 | 0.31* | 0.26* | 0.22 | 0.27 |
| 56 TB− | 0.68* | 0.42 | 0.90* | 0.60* | 0.31 | 0.73* |
| 57 TB− | 0.25 | 0.40 | 0.55* | 0.46* | 0.29 | 0.37 |
| 58 TB− | 0.25 | 0.32 | 0.44* | 0.46* | 0.28 | 0.41 |
| 59 TB− | 0.33* | 0.30 | 0.65* | 0.49* | 0.25 | 0.45 |
| 60 TB− | 0.37* | 0.36 | 0.62* | 0.53* | 0.29 | 0.44 |
| 61 TB− | 0.52* | 0.36 | 0.76* | 0.69* | 0.34 | 0.41 |
| 62 TB− | 0.19 | 0.26 | 0.19 | 0.27* | 0.35* | 0.30 |
| 63 TB− | 0.16 | 0.21 | 0.26* | 0.27* | 0.22 | 0.25 |
| 64 TB− | 2.50* | 2.33* | 0.37* | 4.00* | 3.98* | 0.29 |
| cut-off | 0.27 | 0.45 | 0.25 | 0.25 | 0.35 | 0.70 |
| Sensitivity | 100 | 100 | 100 | 100 | 100 | 100 |
| Specificity | 47 | 64 | 20 | 18 | 67 | 80 |

Example 6

A set of 64 samples of serum from patients attending a clinic with suspected TB (tuberculosis) in a high burden TB population was examined using ELISA. Samples 1-9 had been diagnosed as positive for infection with tuberculosis (TB+) on the basis of a range of assays including sputum smear and culture, and samples 10-64 as negative for infection with tuberculosis (TB−). An ELISA assay was carried out with three synthetic antigens having the structures:

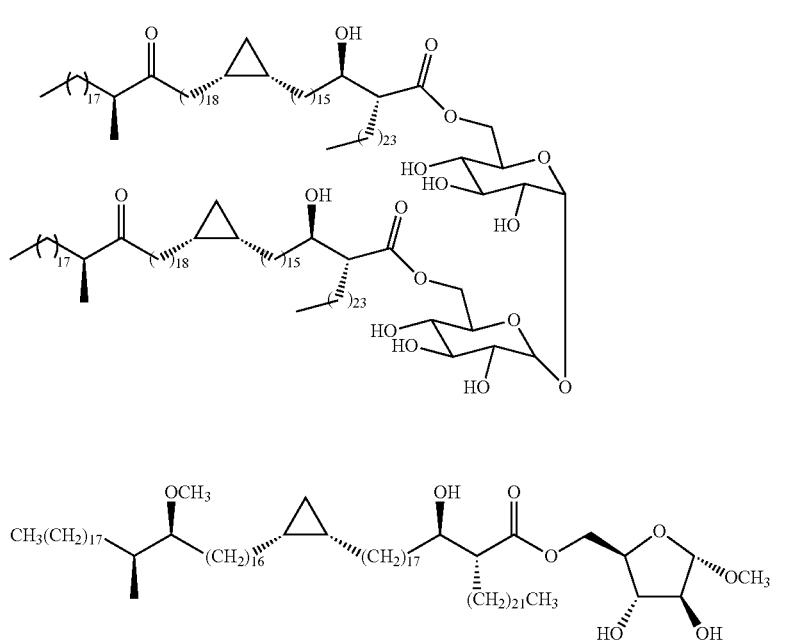

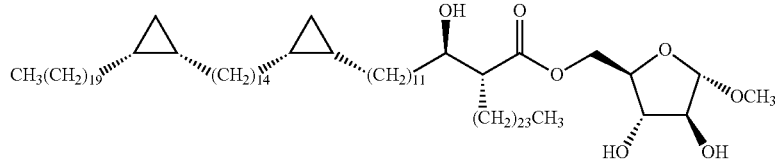

3

Cut-off values were set to identify all the positive samples with all three antigens, and the false positives were then identified in Table 3. By characterising a false positive as above the cut-off for all three antigens, the sensitivity was found to be 100%. 53 of the 55 negatives were correctly identified giving a specificity of 96%. The shaded results denote a result which is above the cut-off set for that particular antigen assay.

TABLE 3

| Sample (diagnosis in brackets) | Antigens | | |
|---|---|---|---|
| | 1 | 2 | 3 |
| | Dilution | | |
| | 1 in 20 | 1 in 80 | 1 in 80 |
| 1 (TB+) | 2.95* | 0.42* | 0.74* |
| 2 (TB+) | 4.41* | 0.36* | 0.76* |
| 3 (TB+) | 3.66* | 0.77* | 0.99* |
| 4 (TB+) | 3.92* | 0.90* | 0.97* |
| 5 (TB+) | 3.31* | 0.38* | 0.99* |
| 6 (TB+) | 4.22* | 0.54* | 1.39* |
| 7 (TB+) | 3.55* | 1.15* | 1.97* |
| 8 (TB+) | 3.88* | 0.69* | 1.67* |
| 9 (TB+) | 1.31* | 0.56* | 1.09* |
| 10 (TB−) | 0.39 | 0.35 | 0.59 |
| 11 (TB−) | 0.71 | 0.45* | 0.92* |
| 12 (TB−) | 4.06* | 0.29 | 0.84* |
| 13 (TB−) | 0.64 | 0.34 | 0.60 |
| 14 (TB−) | 1.25 | 0.58* | 1.30* |
| 15 (TB−) | 0.60 | 0.37* | 0.64 |
| 16 (TB−) | 0.21 | 0.42* | 0.56 |
| 17 (TB−) | 1.54* | 0.47* | 0.81* |
| 18 (TB−) | 0.36 | 0.25 | 0.68 |
| 19 (TB−) | 1.17 | 0.31 | 0.71* |
| 20 (TB−) | 0.51 | 0.38* | 1.03* |
| 21 (TB−) | 0.55 | 0.35 | 0.61 |
| 22 (TB−) | 2.53* | 0.24 | 0.66 |
| 23 (TB−) | 0.33 | 0.35* | 0.81* |
| 24 (TB−) | 1.66* | 0.26 | 0.62 |
| 25 (TB−) | 0.19 | 0.18 | 0.21 |
| 26 (TB−) | 0.62 | 0.24 | 0.72* |
| 27 (TB−) | 0.55 | 0.33 | 0.61 |
| 28 (TB−) | 0.30 | 0.23 | 0.38 |
| 29 (TB−) | 0.31 | 0.29 | 0.41 |
| 30 (TB−) | 0.36 | 0.24 | 0.39 |
| 31 (TB−) | 0.45 | 0.30 | 0.51 |
| 32 (TB−) | 1.29 | 0.57* | 0.91* |
| 33 (TB−) | 0.52 | 0.46* | 0.42 |
| 34 (TB−) | 0.46 | 0.51* | 0.49 |
| 35 (TB−) | 0.39 | 0.26 | 0.38 |
| 36 (TB−) | 0.25 | 0.23 | 0.28 |
| 37 (TB−) | 1.32* | 0.41* | 0.55 |
| 38 (TB−) | 0.81 | 0.40* | 0.52 |
| 39 (TB−) | 0.27 | 0.31 | 0.35 |
| 40 (TB−) | 0.41 | 0.25 | 0.35 |
| 41 (TB−) | 0.23 | 0.33 | 0.66 |
| 42 (TB−) | 2.97* | 0.42* | 0.55 |
| 43 (TB−) | 0.50 | 0.29 | 0.30 |
| 44 (TB−) | 2.34* | 0.67* | 0.98* |
| 45 (TB−) | 0.74 | 0.35* | 0.43 |
| 46 (TB−) | 0.32 | 0.26 | 0.31 |
| 47 (TB−) | 0.55 | 0.41* | 0.56 |
| 48 (TB−) | 0.92 | 0.17 | 0.32 |
| 49 (TB−) | 0.49 | 0.25 | 0.51 |

TABLE 3-continued

| Sample (diagnosis in brackets) | Antigens | | |
|---|---|---|---|
| | 1 | 2 | 3 |
| | Dilution | | |
| | 1 in 20 | 1 in 80 | 1 in 80 |
| 50 (TB−) | 2.37* | 0.30 | 0.37 |
| 51 (TB−) | 1.66* | 0.18 | 0.21 |
| 52 (TB−) | 0.54 | 0.26 | 0.36 |
| 53 (TB−) | 0.87 | 0.25 | 0.26 |
| 54 (TB−) | 2.11* | 0.20 | 0.27 |
| 55 (TB−) | 0.39 | 0.22 | 0.27 |
| 56 (TB−) | 0.65 | 0.31 | 0.73* |
| 57 (TB−) | 1.39* | 0.29 | 0.37 |
| 58 (TB−) | 0.41 | 0.28 | 0.41 |
| 59 (TB−) | 1.11 | 0.25 | 0.45 |
| 60 (TB−) | 1.16 | 0.29 | 0.44 |
| 61 (TB−) | 0.63 | 0.34 | 0.41 |
| 62 (TB−) | 1.64* | 0.35* | 0.30 |
| 63 (TB−) | 0.48 | 0.22 | 0.25 |
| 64 (TB−) | 4.32* | 3.98* | 0.29 |
| Individual Sensitivity | 89 | 100 | 100 |
| Individual Specificity | 87 | 67 | 80 |

Example 7

Selective cytokine stimulation was demonstrated as follows:

The concentrations of cytokines in the cell-free medium from stimulation of bone marrow-derived dendritic cells were determined using standard cytokine-specific ELISA. BMDCs were generated from mice, by flushing out the femurs of mice into complete medium and pipetting vigorously to make a single-cell suspension. The glycolipids were coated to the bottom of 96 micro-well plates (100 μg/ml). BMDCs were added, and after 6 or 48 hours of incubation the supernatants were harvested.

The first experiment was the IL-6 secretion by wild-type BMDCs from mice using compounds B, D, C and H (shown below) as antigens at 100 μg/ml, and isopropyl alcohol (ISO) as a solvent. Commercial trehalose-6,6-dimycolate (TDM), lipopolysaccharides (LPS), and trehalose-6,6-dibehenate (TDB) were used as a controls. The results (illustrated in FIG. 1) showed that compound D stimulated the BMDCs to produce IL-6 to a very high level, in comparison to LPS. Compounds B and H also showed a good level of stimulation, while for compound C no significant stimulation was observed.

B. 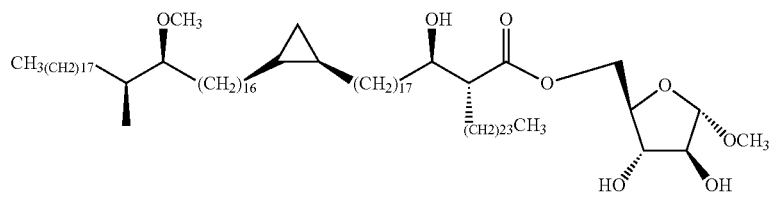
C. 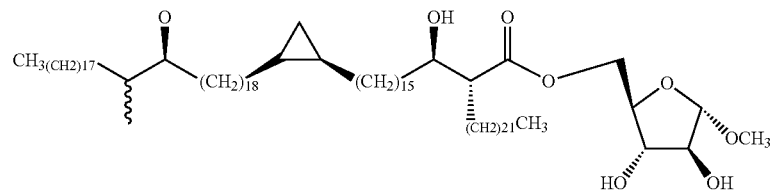
D. 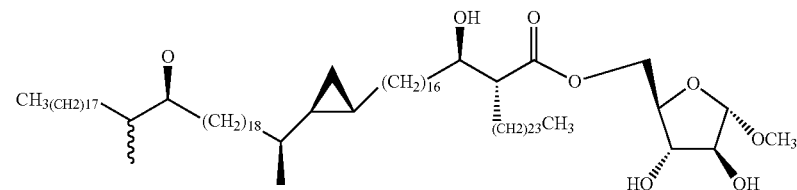
H. 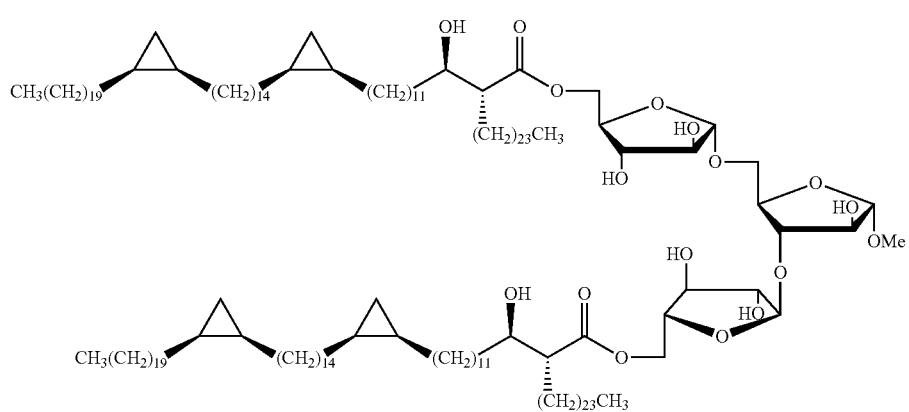

The second experiment measured IL-1β secretion by wild-type BMDCs (un-primed cells) with an incubation time of 48 h with the antigens at 100 µg/ml, and ISO as solvent. Compound I was also tested:

I.

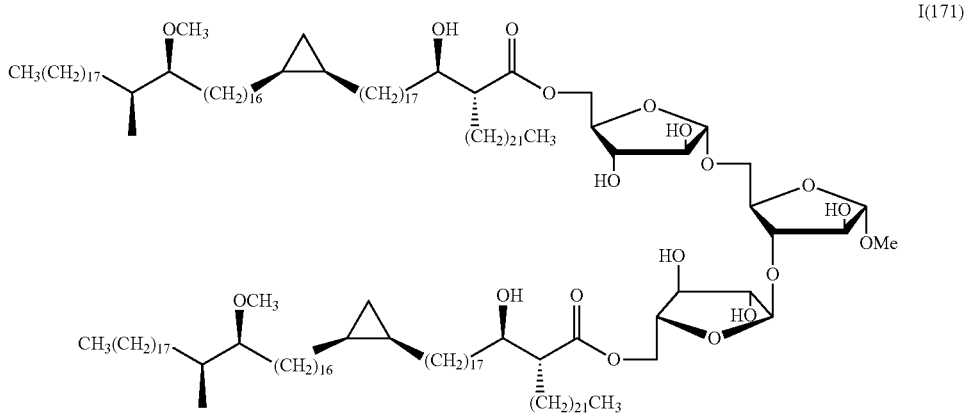

Figure 2:
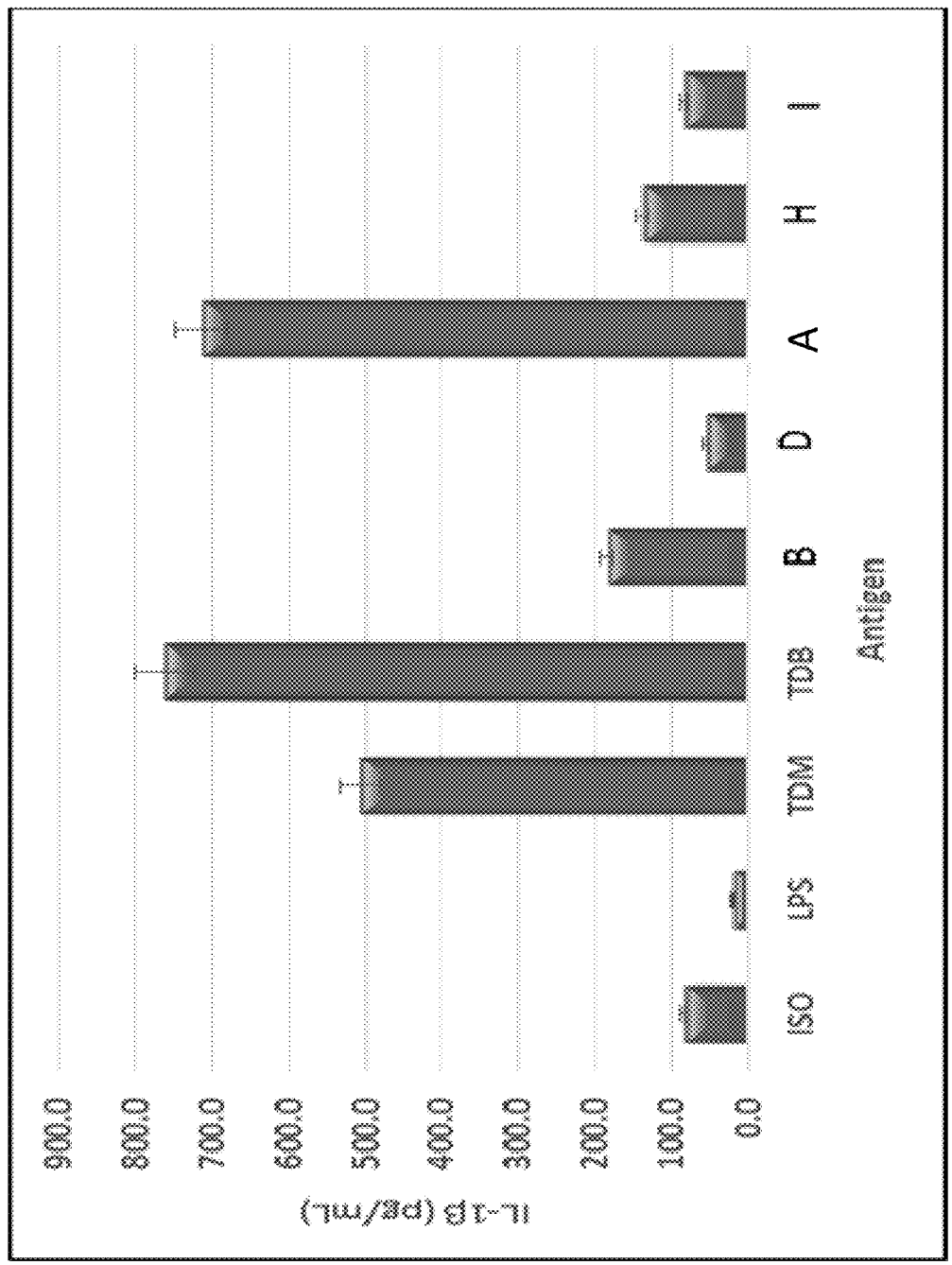
FIG. 2 shows the experimental results of measured IL-1β secretion by wild-type BMDCs using compounds B, D, A, H and I as antigens and isopropyl alcohol (ISO) as a solvent. Commercial TDM, LPS, and TDB were used as a controls. Commercial TDM, LPS, and TDB were used as controls.

Commercial TDM, LPS, and TDB were used as controls. FIG. 2 again shows selective stimulation depending on the antigen structure.

The invention claimed is:

1. A method of determining whether an individual is infected with a mycobacterial disease, the method comprising:
   (a) providing a system which comprises a synthetic antigen which is an arabinose ester of a mycolic acid of formula (III):

 (III)

wherein x is from 1 to 6, y is from 1 to 12, z is from 0 to 10, each M and each M' is independently a mycolic acid moiety including a β-hydroxy acid moiety and each S is a monosaccharide unit, provided that at least one S is an arabinose unit;
   (b) contacting the system with a sample obtained from the individual; and
   (c) detecting the presence or absence of binding of a biomarker in the sample with the synthetic antigen, wherein the biomarker is an antibody indicative of infection with or exposure to mycobacteria and wherein step (c) involves contacting the system with a composition comprising a secondary antibody configured to interact with the biomarker, wherein either:
      (i) the secondary antibody is carried by colloidal gold particles: or
      (ii) the secondary antibody is bound to an enzyme, wherein the method further comprises adding a composition comprising a colorimetric substrate to the system and wherein the colorimetric substrate undergoes a color change on reaction with the enzyme, and wherein step (c) includes detecting the presence of binding of the biomarker in the sample with the synthetic antigen when the secondary antibody interacts with the biomarker.

2. A method according to claim 1 wherein steps (a), (b) and (c) are carried out in the order (a) followed by (b) followed by (c).

3. A method according to claim 1 wherein the synthetic antigen is present on a substrate in the system and/or in one or more solutions or suspensions in the system, and/or is encapsulated in the system.

4. A method according to claim 1 wherein the system comprises a substrate which carries the synthetic antigen.

5. A method according to claim 1 wherein the synthetic antigen is selected from the following classes of compounds:
   (i) salts of mycolic acids;
   (ii) esters of synthetically prepared mycolic acids;
   (iii) sulfur-containing mycolic acids and/or salts or esters thereof; and
   (iv) mycolic acid wax esters or salts thereof.

6. A method according to claim 4, wherein step (c) involves contacting the substrate with a composition comprising colloidal gold particles wherein the colloidal gold particles carry the secondary antibody.

7. A kit for determining the presence or absence of a biomarker in a sample, the kit comprising:
   a system which comprises a synthetic antigen which is an arabinose ester of a mycolic-acid of formula (III):

 (III)

wherein x is from 1 to 6, y is from 1 to 12, z is from 0 to 10, each M and each M' is independently a mycolic acid moiety including a β-hydroxy acid moiety and each S is a monosaccharide unit, provided that at least one S is an arabinose unit; and
   a composition comprising a secondary antibody configured to interact with the biomarker,
   wherein the biomarker is an antibody indicative of infection with or exposure to mycobacteria.

8. A composition comprising at least 90 wt % of a single compound selected from compounds having the formula A, B, C, D, E, F, G, H, or I:

A.
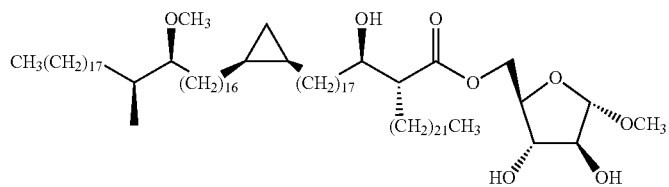
B.
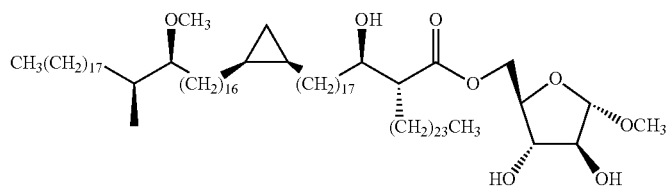
C.
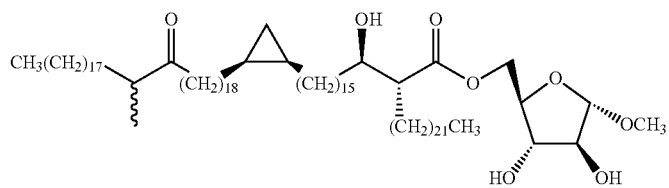
D.
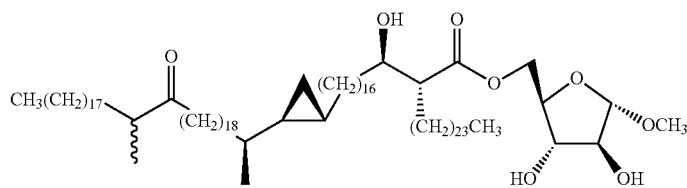
E.
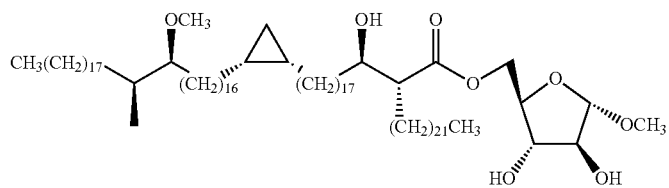
F.
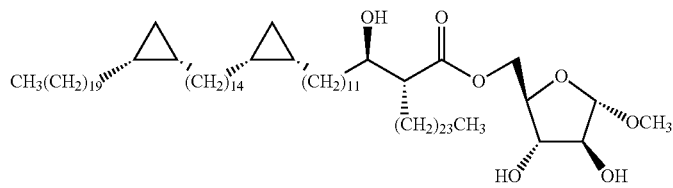

-continued
G.
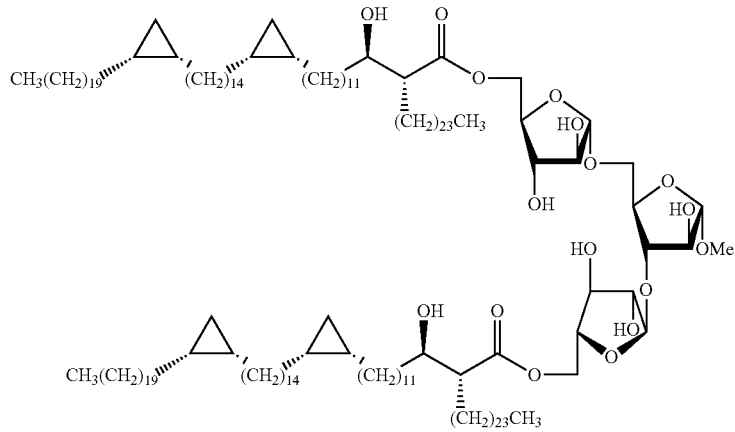
H.
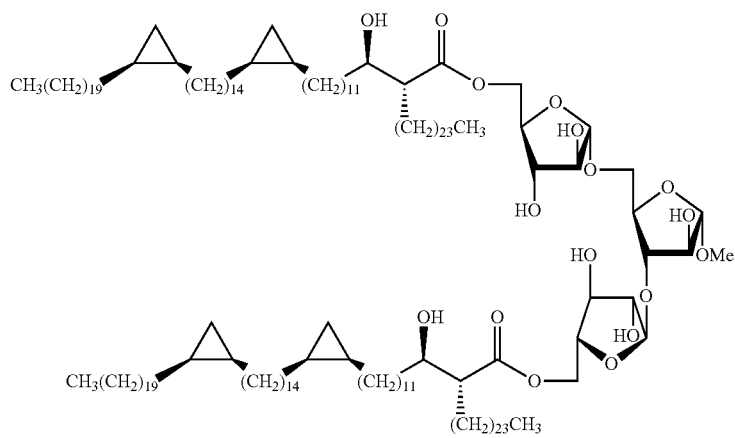
I.
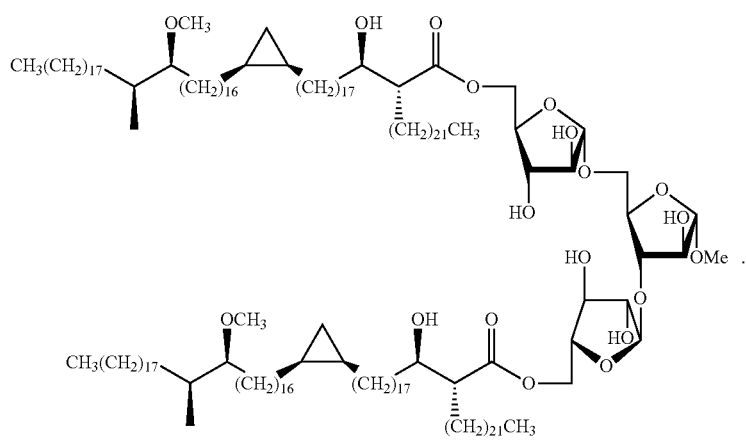
* * * * *